United States Patent [19]

Rzeszotarski et al.

[11] Patent Number: 5,395,827

[45] Date of Patent: Mar. 7, 1995

[54] ω-[2-(PHOSPHONOALKYL)PHENYL]-2-AMINOALKANOIC ACIDS AS ANTAGONISTS OF EXCITATORY AMINO ACID RECEPTORS

[75] Inventors: Waclaw J. Rzeszotarski, Millersville; Suzanne R. Ellenberger, Reisterstown; Maria E. Guzewska, Pasadena; John W. Ferkany, Baltimore; Gregory S. Hamilton, Catonsville; Raymond J. Patch, Baltimore; Edward W. Karbon, Jr, Ellicott City, all of Md.

[73] Assignee: Guilford Pharmaceuticals Inc., Baltimore, Md.

[21] Appl. No.: 171,629

[22] Filed: Dec. 22, 1993

Related U.S. Application Data

[63] Continuation of Ser. No. 765,470, Sep. 26, 1991, abandoned, which is a continuation-in-part of Ser. No. 639,231, Jan. 9, 1991, abandoned, which is a continuation of Ser. No. 225,845, Jul. 29, 1988, abandoned, which is a continuation-in-part of Ser. No. 936,280, Dec. 1, 1986, abandoned, which is a continuation of Ser. No. 849,696, Apr. 9, 1986, Pat. No. 4,657,899.

[51] Int. Cl.$^6$ ............... C07F 9/38; A61K 31/66
[52] U.S. Cl. .................. 514/114; 558/190; 558/193; 560/20; 560/22; 560/23; 560/38; 560/40; 562/11
[58] Field of Search ............... 562/11; 560/20-23, 560/38, 39, 40; 514/113, 114, 119; 558/190, 192, 193

[56] References Cited

U.S. PATENT DOCUMENTS 4,657,899  4/1987  Rzeszotarski et al. ............... 514/120

(List continued on next page.)

FOREIGN PATENT DOCUMENTS 432994  6/1991  European Pat. Off. .

OTHER PUBLICATIONS

Watkins et al., "Excitatory Amino Acid Transmitters," *Amer. Rev. Pharmacol. Toxicol.* (1981), vol. 21, pp. 165–204.

(List continued on next page.)

*Primary Examiner*—Joseph E. Evans
*Attorney, Agent, or Firm*—Nath, Amberly & Associates

[57]  ABSTRACT

The present invention pertains to antagonists of excitatory amino acid neurotransmitter receptor antagonists, their method of preparation as well as compositions containing them which have the general formula:

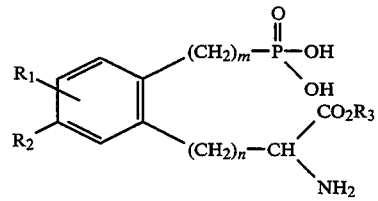

wherein n and m independently are 0, 1, 2, or 3; $R_1$ is selected from the group consisting of hydrogen and $R_2$; $R_2$ is selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl, wherein if $R_2$ is hydrogen, $R_1$ is not hydrogen; $R_3$ is selected from the group consisting of hydrogen and $C_1$ to $C_6$ lower alkyl; the stereoisomers thereof in their resolved or racemic form, and pharmaceutically acceptable salts thereof.

19 Claims, No Drawings

U.S. PATENT DOCUMENTS

| | | |
|---|---|---|
| 4,761,405 | 8/1988 | Rzeszotarski et al. ............... 514/114 |
| 4,822,780 | 4/1989 | Tsuda et al. ......................... 514/119 |
| 4,918,064 | 4/1990 | Cordi et al. ......................... 514/114 |
| 5,049,555 | 9/1991 | Rzeszotarski et al. ............... 514/114 |
| 5,162,311 | 11/1992 | Herrling et al. ..................... 514/114 |
| 5,175,153 | 12/1992 | Bigge et al. ......................... 514/114 |

OTHER PUBLICATIONS

Schwarcz et al., "Quinolinic Acid" An Endogenous Metabolite that Produces Axon–Sparing Lesions in Rat Brain,: *Science*, Jan. 1983, vol., 219, pp. 316–318.

Simon et al., "Blockage of N–Methyl–D–Aspartate Receptors May Protect Against Ischemic Damage in the Brain," *Science*, vol. 226, pp. 850–852. Nov., 1984.

Foster et al., "Acidic Amino Acid Binding Sites in Mammalian Neuronal Membranes: Their Characteristics and Raltionship to Synaptic Receptors,"*Brain Research* Reviews, vol. 7 (1984), pp. 103–164.

Schoepp et al., "Pharmacological and Functional Characteristics of Metabotropic Excitatory Amino Acid Receptors," *Tr. Pharmacol. Sci.*, Special Report (1991), pp. 74–81.

Faden et al., "Effects of Competitive and Non–Competitive NMDA Receptor Antagonists in Spinal Cord Injury," European Journal of Pharmacology, vol. 175 (1990), pp. 165–174.

Frandsen et al., "Direct Evidence that Excitotoxicity in Cultured Neurons is Mediated via N–Methyl–D–Aspartate (NMDA) as well as Non–NMDA Receptors," *Journal of NeuroChemistry*, vol. 53, No. 1, 1989, pp. 297–299.

Sheardown et al., "2, 3–Dihydroxy–6–nitro–7–sulfamoyl–benzo(F)quinoxaline: A Neuroprotectant for Cerebral Ischemica," *Science*, vol. 247, Feb. 1990, pp. 571–574.

Costa, "Allosteric Modulatory Centers of Transmitter Amino Acid Receptors," *Neuropsychopharmacology*, vol. 2, No. 3 (1989), pp. 167–174.

Matoba et al., "Structural Modification of Bioactive Compounds, II: Syntheses of Aminophosphonoic Acid," *Chem. Pharm. Bulletin*, vol. 32 (1984), pp. 3918–3925.

Lodge et al. [Eds.], "The Pharmacology of Excitatory Amino Acids," *Elsevier Trends Journals* (1991), pp. 1–89.

ω-[2-(PHOSPHONOALKYL)PHENYL]-2-AMINOALKANOIC ACIDS AS ANTAGONISTS OF EXCITATORY AMINO ACID RECEPTORS

CROSS-REFERENCE TO RELATED APPLICATIONS

The present application is a continuation of U.S. Ser. No. 07/765,470, filed Sep. 26, 1991, now abandoned, which is a continuation-in-part of U.S. Ser. No. 07/639,231, filed Jan. 9, 1991, and now abandoned, which is a continuation of U.S. Ser. No. 07/225,845, filed Jul. 29, 1988, and now abandoned, which is a continuation-in-part of U.S. Ser. No. 06/936,280, filed Dec. 1, 1986, and now abandoned, which is a continuation of U.S. Ser. No. 06/849,696, filed Apr. 9, 1986, now U.S. Pat. No. 4,657,899, the contents of which are all incorporated herein by reference.

BACKGROUND OF THE INVENTION

1. Field of the Invention:

The present invention pertains to novel non-N-methyl-D-aspartic acid excitatory amino acid (EAA) antagonists and particularly to novel, potent and selective antagonists of kainic acid (KA) and AMPA-type [(RS)-alpha-aminomethyl-3-hydroxy-5-methylisoxazole propionic acid] EAA receptors having anxiolytic, anticonvulsant, antiepileptic, analgesic, antiemetic, neuroprotective and cognition enhancing actions achieved through the antagonisms of these receptors. In particular, the invention is directed to: 2-[omega-phosphonoalkyl)phenyl]- 2-aminoalkanoic acids and their interaction with KA and AMPA receptors, their pharmaceutically acceptable salts, and to uses thereof.

2. Description of the Prior Art:

Excitatory amino acids (EAA) mediate a substantial portion of the chemical synaptic activity occurring in the central nervous system. Current understanding recognizes at least three major ionotropic receptors for EAAs. Most commonly identified by protypical agonists, these include:

(1) receptors activated by AMPA [(RS)-alpha-aminomethyl-3-hydroxy-5-methylisoxazole propionic acid], a cyclic analog of L-glutamate (GLU), (2) receptors recognizing the pyrrolidine neurotoxin kainic acid (KA), and (3) receptors responding to N-methyl-D-aspartate (NMDA), a synthetic analog of L-aspartate [D. R. Curtis, A. W. Duggar, D. Felix, G. A. R. Johnston, A. K. Tebecis and J. C. Watkins, Brain Res., 41, 283–301 (1972); J. C. Watkins and R. H. Evans., Ann. Rev. Pharmacol. Toxicol., 21, 165–204 (1981); A. C. Foster and G. Fagg, Brain Res. Rev. 7, 103–164 (1984)]. In addition to these major channel-linked receptors, evidence now suggests the presence of "metabotropic" EAA receptors which directly activate second messenger responses [D. Schoepp, J. Bockaert and F. Sladeczek, IN C. Lodge and G. L. Collingridge (eds.) Tr. Pharmacol. Sci., Special Report, "The Pharmacology of Excitatory Amino Acids," Elsevier, Cambridge, UK., pages 74–81, (1991)]. Furthermore, it is now apparent that the NMDA-mediated ionotropic responses are subject to complex regulatory influences and, that this particular recognition site may exist as a supramolecular entity similar to the GABA/benxodiazepine/barbiturate effector proteins [E. Costa, Neuropsychopharmacology, 2, pages 167–174 (1989)].

In general, EAA agonists are potent convulsants in animal models. Additionally, AMPA, KA and the endogenous NMDA agonist, quinolinic acid (QUIN) and the mixed ionotropic/metabotropic agonist ibotenic acid have been used to produce laboratory models of neurodegenerative disorders [K. Biziere, J. T. Slevin, R. Zaczek, J. S. Collins and J. T. Coyle. IN H. Yoshida, Y. Hagihara and S. Ebashi (eds.), "Advances in Pharmacology and Therapeutics," Pergamon, N.Y., 1982, pp. 271–276; R. Schwarcz, W. O. Whetsell and R. M. Mango, Science, 219, pages 316–318 (1983)]. It has been suggested for some time that a dysfunction in EAA neurotransmission may contribute to the neuropathology associated with the epilepsies and neurodegenerative conditions [B. Meldrum and M. Williams (eds.), "Current and Future Trends in Anticonvulsant, Anxiety and Stroke Therapy," Wiley Liss, New York, (1990)].

The development of selective NMDA antagonists has further expanded the understanding of EAA neurotransmission, physiology and pathophysiology in the mammalian brain. In particular, substantial preclinical evidence is now available suggesting that NMDA receptor antagonists may be useful as anxiolytics, anticonvulsants, antiemetics [European Patent Application No. 432,994], antipsychotics or muscle relaxants, and that these compounds may prevent or reduce neuronal damage in instances of cerebral ischemia, hypoxia, hypoglycemia or trauma [R. P. Simon, J. H. Swan, T. Griffiths and B. S. Meldrum, Science, 226, pages 850–852 (1984); D. N. Stephens, B. S. Meldrum, R. Weidman, C. Schneider and M. Grutzner, Psychopharmacology, 90, pages 166–169 (1986); D. Lodge and G. L. Collingridge (eds.) "The Pharmacology of Excitatory Amino Acids," Elsevier Trends Journals, Cambridge, UK. (1991); A. I. Fader, J. A. Ellison and L. J. Noble, Eur. J. Pharmacol., 175, pages 165–174 (1990)].

Given the broad therapeutic potential of EAA antagonists, it is not surprising that efforts have been initiated to identify additional antagonist compounds. While there has been substantial success in finding competitive and non-competitive antagonists of NMDA receptors, there are few reports of potent and selective antagonists of KA or AMPA-type EAA receptors [J. C. Watkins, P. Krogsgaard-Larsen and T. Honore, IN D. Lodge and G. L. Collingridge (eds.), "The Pharmacology of Excitatory Amino Acids," Elseiver Trends Journals, Cambridge, UK., pages 4–12 (1991); M. J. Sheardow, E. O. Nielsen, A. J. Hansen, P. Jacobsen and T. Honore, Science, 247, pages 571–573 (1990); A. Frasden, J. Drejer and A. Shousboe, J. Neurochem., 53, pages 297–300 (1989)]. Identification of such antagonists is important since these agents are expected to share many of the potential therapeutic actions of antagonists of NMDA-type EAA receptors.

In the past, 2-amino-4-(2-phosphonomethylphenyl)-butyric acid has been reported by Matoba et al. [Chem. Pharm. Bull. 32, pages 3918–3925 (1984)]. More particularly, Matoba et al. prepared several amino-phosphonoic acids and notably, 2-amino-5-phosphonopentanoic acid, 2-amino-4-(2-amino-5-phosphonomethylphenyl)butyric acid, 2-(2-amino-2-carboxy) ethylphenyl-phosponic acid and N-benzylproline-4-phosphonic acid. One of the target compounds, 2-amino-4-(2-phosphonomethylphenyl)butyric acid was synthesized starting with (2-bromomethyl)phenethylbromide. This dibromide was treated with triethyl phosphite to give diethyl (2-(2-bromoethylphenyl)methylphosphonate, and this bromophosphonate derivative was treated with sodium diethyl acetamidomalonate to give the expected acetamidomalonylphosphonate derivative which was purified through a silica gel column. It should be pointed out that none of the Matoba el al. compounds contain substituents on the benzene ring.

Other related compounds having NMDA antagonist activity have been reported in Rzeszotarski et al., U.S. Pat. No. 4,657,899. In particular, Rzeszotarski et al. disclose potent and selective EAA neurotransmitter receptor antagonists having the general formula:

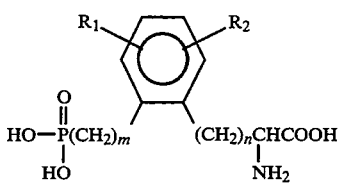

wherein $R_1$ and $R_2$ are the same or different and are selected from the group consisting of hydrogen, lower alkyl, halogen, amino, nitro, trifluoromethyl or cyano, or taken together are —CH=CH—CH=CH—; n and m=0, 1, 2, or 3; and the pharmaceutically acceptable salts and the 2-acetamido-2-carboethoxy esters thereof. Rzeszotarski et al. also disclose specific compounds, including 2-amino-3-[2-(2-phosphonoethyl)phenyl]-propanoic acid, 2-amino-3-[2-(3-phosphonopropyl)-phenyl]propanoic acid, 2-amino-5-[2-phosphonome-thylphenyl]pentanoic acid, and 2-amino-3-[2-phosphonomethylphenyl]propanoic acid which are disclosed as antagonists of NMDA and show very low binding affinity for kainate receptors; see Table I on column 13. The valuable pharmacological properties of the present new compounds are particularly surprising in view of the compounds disclosed and described in U.S. Pat. No. 4,657,899.

SUMMARY OF THE INVENTION

The present invention provides a potent, selective excitatory amino acid kainic acid receptor antagonist compound having the general formula:

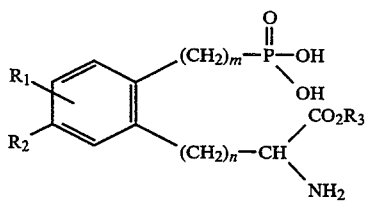

wherein n and m independently is 0, 1, 2, or 3; $R_1$ is selected from the group consisting of hydrogen and $R_2$; $R_2$ is selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl, wherein if $R_2$ is hydrogen, $R_1$ is not hydrogen; $R_3$ is selected from the group consisting of hydrogen, and $C_1$ to $C_6$ lower alkyl; the stereoisomers thereof in their resolved or racemic form, and pharmaceutically acceptable salts thereof.

More particularly the invention provides a potent, selective excitatory amino acid kainic acid receptor antagonist compound having the general formula:

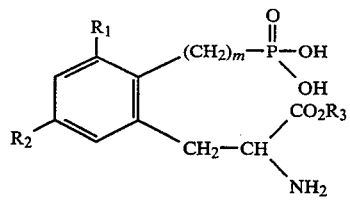

wherein m is 2 or 3; $R_1$ is selected from the group consisting of hydrogen, methyl and halogen; $R_2$ is selected from the group consisting of halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl; $R_3$ is selected from the group consisting of hydrogen, and $C_1$ to $C_6$ lower alkyl; the stereoisomers thereof in their resolved or racemic form, and pharmaceutically acceptable salts thereof.

Another aspect of the invention involves use of the pharmaceutical compositions for relieving pain, treatment of convulsions or epilepsy, enhancing cognition, treating psychosis, preventing neurodegeneration, treating cerebral ischemic or trauma-induced damage, and treating emesis.

A further aspect of the invention involves a method for antagonizing excitatory amino acid kainic acid or AMPA receptors by utilizing a compound having the general formula:

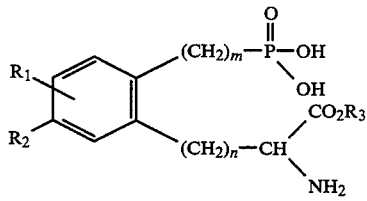

wherein n and m independently are 0, 1, 2, or 3; $R_1$ is selected from the group consisting of hydrogen and $R_2$; $R_2$ is selected from the group consisting of halogen, halomethyl, nitro, amino, alkoxy, hydroxyl, hydroxymethyl, $C_1$ to $C_6$ lower alkyl, to $C_7$ to $C_{12}$ higher alkyl, aryl and aralkyl; is selected from the group consisting of hydrogen, and $C_1$ to $C_6$ lower alkyl; the stereoisomers thereof in their resolved or racemic form, and pharmaceutically acceptable salts thereof.

Preferred compounds according to the invention include:
5-methyl-2-(2-phosphonoethyl)phenylalanine;
5-phenyl-2-(2-phosphonoethyl)phenylalanine;
3-phenyl-2-(2-phosphonoethyl)phenylalanine hydrochloride;
5-ethyl-2-(2-phosphonoethyl)phenylalanine;
5-bromo-2-(2-phosphonoethyl)phenylalanine;
5-fluoro-2-(2-phosphonoethyl)phenylalanine;
5-chloro-2-(2-phosphonoethyl)phenylalanine;
5-iodo-2-(2-phosphonoethyl)phenylalanine;
5-methoxy-2-(2-phosphonoethyl)phenylalanine;
3,5-dimethyl-2-(2-phosphonoethyl)phenylalanine;
5-amino-2-(2-phosphonoethyl)phenylalanine;
5-hydroxymethyl-2-(2-phosphonoethyl)phenylalanine;
5-hydroxy-2-(2-phosphonoethyl)phenylalanine;
4-nitro-2-(2-phosphonoethyl)phenylalanine;
5-nitro-2-(2-phosphonoethyl)phenylalanine;
5-trifluoromethyl-2-(2-phosphonoethyl)phenylalanine;
4,5-dichloro-2-(2-phosphonoethyl)phenylalanine; and 5-methyl-2-(3-phosphonopropyl)phenylalanine.

DETAILED DESCRIPTION OF THE INVENTION

The structure and formulation of the novel compounds of the invention was the result of an extensive research investigation into the antagonism of excitatory amino acid kainic acid and AMPA neurotransmitter receptors.

It is generally accepted that L-glutamic acid (GLU), a dicarboxylic amino acid, is the principal excitatory amino acid neurotransmitter in the mammalian central nervous system (CNS). Ion channel-linked or "ionotropic" excitatory amino acid receptor subtypes include those selectively activated by N-methyl-D-aspartic acid (NMDA), α-amino-3-methyl-4-isoxazole propionic acid (AMPA), and kainic acid (KA). A "metabotropic" GLU receptor coupled to phospholipid metabolism and a putative GLU autoreceptor have also been identified.

L-glutamic acid is believed to have an important physiological role in the functioning of the CNS since a great majority of CNS neurons utilize GLU as their neurotransmitter. In addition, the diversity of receptor subtypes with which GLU interacts contributes to its ability to elicit a variety of synaptic events. Ionotropic GLU receptors mediate fast excitatory postsynaptic potentials and contribute to the architectural development and plasticity of excitatory synapses. Metabotropic GLU receptors are considered to play primarily a neuromodulatory role, although simultaneous activation of ionotropic and metabotropic receptors might be required for the development of neuronal plasticity at certain CNS synapses.

Because of its involvement in excitatory neurotransmission, GLU has been suggested to have a role in CNS conditions characterized by heightened neuronal activity or sensitivity including epilepsy, ischemia or trauma-induced neuronal damage, and certain neurologic and neurodegenerative disorders. Accordingly, pharmacological manipulation of GLU receptors is therapeutically useful in the treatment of several CNS disorders and diseases.

The NMDA receptor is the most well-characterized GLU receptor subtype because of the availability of selective antagonists. D(−)-2-amino-5-phosphonopentanoic acid (AP-5) and D(−)-2-amino-5-phosophoheptanoic acid (AP-7) were among the first NMDA antagonists identified and act competitively by binding to the GLU recognition site.

Competitive NMDA antagonists have been demonstrated to possess therapeutic potential as anticonvulsant and cerebroprotective agents. However, a growing body of evidence suggests that blockage of non-NMDA receptors, particularly KA and AMPA receptors, might also be useful in the treatment of CNS disorders involving glutamatergic neurotransmission. In support of this hypothesis, KA-induced seizures have been used as an animal model of temporal lobe epilepsy in humans, suggesting that KA antagonists might be useful in the management of this CNS disorder. A potential therapeutic use for KA or AMPA antagonists in the treatment of neurodegenerative disorders is indicated by the finding that intrastriatal administration of kainic acid produces a pattern of neuronal damage in rats similar to that observed in Huntington's Disease. Non-NMDA receptors have also been implicated in neurologic disorders including Lathyrism, an upper motor neuron disease characterized by spastic paraparesis, and Guam's Disease, a form of amyotrophic lateral sclerosis.

In contrast to NMDA receptors, a limited number of KA/AMPA receptor antagonists have been described, most of which are non-selective and relatively weak, resulting in an inability to fully characterize the functional and physiological properties of these receptors. However, a series of quinoxalinediones were recently identified as potent non-NMDA antagonists. The therapeutic potential of these compounds is illustrated by their ability to protect against EAA agonist-induced cytotoxicity in cultured cortical neurons and clonic seizures in neonatal rats.

The compounds of the present invention have been identified which competitively antagonize KA and AMPA-induced currents in Xenopus oocytes injected with rat brain mRNA. Members of these compounds have also been shown to possess anticonvulsant properties and to protect against KA-induced striatal toxicity in vivo. These findings are completely unexpected. It has been unexpectedly discovered that these compounds are either phosphonic or dicarboxylic acids and secondly, the compounds do not interact appreciably with high affinity [$^3$H] KA binding sites in rat brain membranes. While the reason for this latter finding is not known, there is considerable controversy regarding the functional relevance of high affinity [$^3$H] KA binding sites since much higher concentrations of KA are required to produce in vitro responses.

The structure and formulation of the novel compounds of this invention relate specifically to excitatory amino acid receptors activated by KA and AMPA for which only a limited number of quinoxalines have been identified as specific antagonists.

The novel compounds provide potent antagonists having greater affinity for KA and AMPA receptors and lesser or no affinity for other CNS receptors, rendering the compounds very selective. This would therefore permit one to selectively antagonize one excitatory amino acid receptor in the tissues also containing other excitatory amino acid receptors. Fewer side effects can be expected as a result of the greater affinity and selectively of the compounds of the present invention.

Preferred compounds of the invention have the formula:

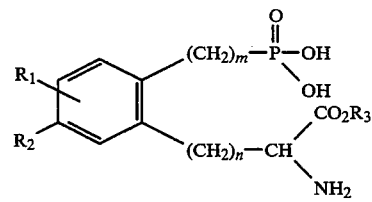

wherein n and m independently is 0, 1, 2, or 3; $R_1$ is selected from the group consisting of hydrogen and $R_2$; $R_2$ is selected from the group consisting of hydrogen, halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl, wherein if $R_2$ is hydrogen, $R_1$ is not hydrogen; $R_3$ is selected from the group consisting of hydrogen, and $C_1$ to $C_6$ lower alkyl; the stereoisomers thereof in their resolved or racemic form, and pharmaceutically acceptable salts thereof, wherein m is preferably 2 and wherein n is preferably 1.

A particularly preferred form of the compound has the formula:

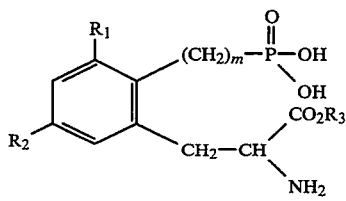

wherein m is 2 or 3; $R_1$ is selected from the group consisting of hydrogen, methyl and halogen; $R_2$ is selected from the group consisting of halogen, halomethyl, nitro, amino, alkoxy, hydroxyl, hydroxymethyl, $C_1$ to $C_6$ lower alkyl, $C_7$ to $C_{12}$ higher alkyl, aryl and aralkyl; $R_3$ is selected from the group consisting of hydrogen, and $C_1$ to $C_6$ lower alkyl; the stereoisomers thereof in their resolved or racemic form, and pharmaceutically acceptable salts thereof.

"Halogen" includes bromo, fluoro, chloro and iodo; "halomethyl" includes mono-, di- and tri-halo groups including trifluoromethyl; amino compounds include amine ($NH_2$) as well as substituted amino groups comprising alkyls of one through six carbons; "aryl" is an aromatic ring compound such as benzene, phenyl, naphthyl and substituted forms thereof; "aralkyl" is an aryl being attached through an alkyl chain, straight or branch, of from one through six carbons.

Particularly preferred specific compounds include:
5-methyl-2-(2-phosphonoethyl)phenylalanine;
5-phenyl-2-(2-phosphonoethyl)phenylalanine;
3-phenyl-2-(2-phosphonoethyl)phenylalanine hydrochloride;
5-ethyl-2-(2-phosphonoethyl)phenylalanine;
5-bromo-2-(2-phosphonoethyl)phenylalanine;
5-fluoro-2-(2-phosphonoethyl)phenylalanine;
5-chloro-2-(2-phosphonoethyl)phenylalanine;
5-iodo-2-(2-phosphonoethyl)phenylalanine;
5-methoxy-2-(2-phosphonoethyl)phenylalanine;
3,5-dimethyl-2-(2-phosphonoethyl)phenylalanine;
5-amino-2-(2-phosphonoethyl)phenylalanine;
5-hydroxymethyl-2-(2-phosphonoethyl)phenylalanine;
5-hydroxy-2-(2-phosphonoethyl)phenylalanine;
5-trifluoromethyl-2-(2-phosphonoethyl)phenylalanine;
4-nitro-2-(2-phosphonoethyl)phenylalanine;
5-nitro-2-(2-phosphonoethyl)phenylalanine;
4,5-dichloro-2-(2-phosphonoethyl)phenylalanine; and
5-methyl-2-(3-phosphonopropyl)phenylalanine.

The preparation of compounds for administration in pharmaceutical preparations may be accomplished in a variety of well known methods known to those skilled in the art of synthetic organic chemistry. Appropriate pharmaceutically acceptable salts within the scope of the invention are those derived from mineral acids such as hydrochloric acid, phosphoric acid, nitric acid and sulfuric acid; and organic acids such as tartaric acid, methanesulfonic acid, benzenesulfonic acid, p-toluenesulfonic acid, and the like, giving the hydrochloride, sulfate, phosphate, nitrate, methanesulfonate, tartrate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm Sci* (1977) 66 (1): 1–19.)

The compounds of the invention contain an asymmetric carbon atom. Thus, the invention includes the individual stereoisomers, and the mixtures thereof. The individual isomers may be prepared or isolated by methods known in the art.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

In the case of oral administration, fine powders or granules of the compound may be formulated with diluents and dispersing and surface active agents, and may be prepared in a draft in water or in a syrup, in capsules or cachets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the pharmaceutical art.

The following examples are illustrative of preferred embodiments of methods of preparation and compounds of the invention and are not to be construed as limiting the invention thereto.

The novel compounds of the invention may be readily prepared by the following synthetic routes:

The 7-iodo isochroman was made from 7-bromoisochroman, as described below.

SCHEME I

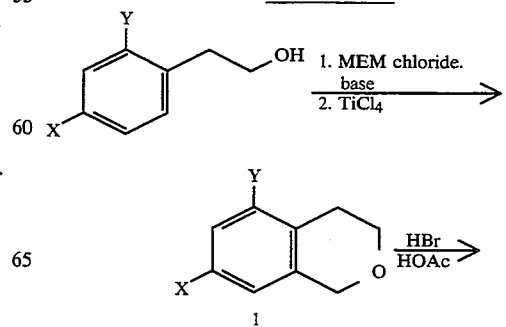

-continued
SCHEME I

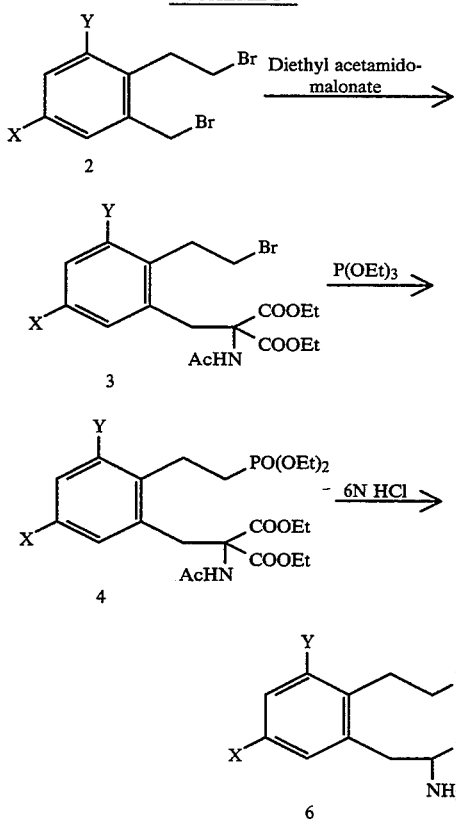

In the case of the 3,5-dimethyl compound, the phenethyl alcohol was prepared from commercially available benzoic acid by the following standard series of reactions:

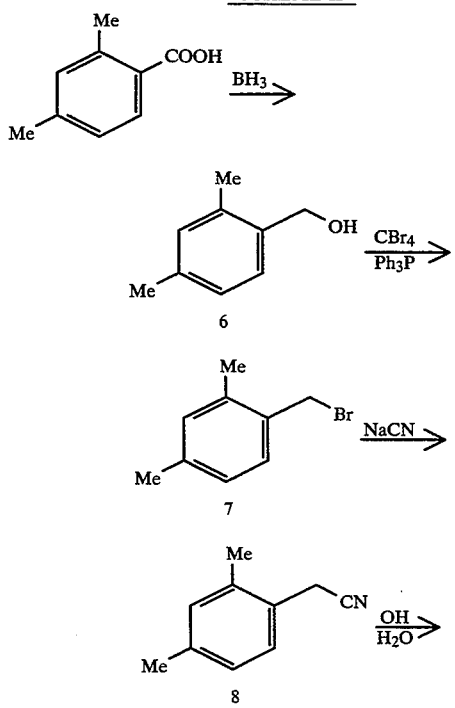

-continued
SCHEME II

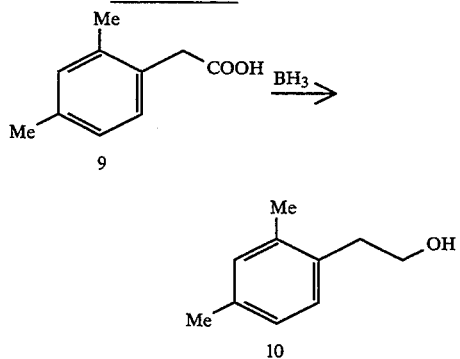

In the case of the 5-nitro compound, the dibromide compound was prepared from 5-nitrohomophthalic acid [W. Borsche, K. Diacont and H. Hanau, Chem. Ber., 67, 675-686 (1934)] according to the following standard series of reactions:

SCHEME III

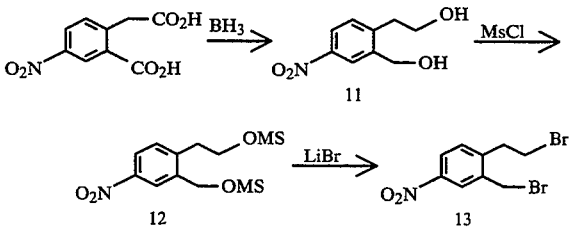

PREPARATION I - SCHEME I

| Compounds | Run | Y Substituents | X Substituents |
| --- | --- | --- | --- |
| 1a | A | H | $CH_3$ |
| 1b | B | H | $C_2H_5$ |
| 1c | C | H | Br |
| 1d | D | H | Cl |
| 1e | E | H | F |
| 1f | F | H | I |
| 1g | G | $CH_3$ | $CH_3$ |

General Procedure for the Synthesis of 7-Substituted Isochromans of compound 1.

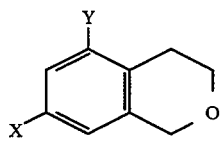

A mixture of the substituted phenethyl alcohol (1 eq), methoxyethoxymethyl (MEM) chloride (1.5 eq) and N,N-diisopropylethylamine (1.5 eq) in dry methylene chloride (2 ml per mmol of phenethyl alcohol) was stirred at room temperature for 2 hours. The reaction mixture was washed with 1N HCl dried ($MgSO_4$) and evaporated. A solution of the crude MEM acetal in dry methylene chloride (1 ml per mmol) was added to a cooled (0° C.) solution of titanium tetrachloride (2 eq) in methylene chloride (10 ml per mmol of acetal). This mixture was stirred at 0° C. for 2 hours and then quenched by the successive addition of methanol (0.2 ml per mmol of acetal) and 3N HCl saturated with sodium chloride (50 ml). The organic phase was dried (MgSO$_4$). The product was purified by column chromatography to give the following 7-substituted isochromans.

RUN A

7-Methylisochroman (1a, 89% yield). $^1$H NMR (CDCl$_3$): δ2.27 (s, 3H); 2.77 (t, 2H); 3.92 (t, 2H); 4.70 (s, 2H); 6.95 (m, 3H). IR (neat): 1244, 1128 cm$^{-1}$.

RUN B

7-Ethylisochroman (1b, 93% yield). $^1$H NMR (CDCl$_3$): δ1.1 (t, 3H); 2.4–2.8 (m, 4H); 3.8 (t, 2H); 4.61 (s, 2H); 6.6–6.9 (m, 3H). IR (neat): 3000, 1223, 1105 cm$^{-1}$.

RUN C

7-Bromoisochroman (1c, 68% yield). $^1$H NMR (CDCl$_3$): δ2.75 (m, 2H); 3.92 (t, 2H); 4.69 (s, 2H); 6.94–7.39 (m, 3H). IR (neat): 2850, 1600, 1480, 1190, 1110, 815 cm$^{-1}$.

RUN D

7-Chloroisochroman (1d, 65% yield). $^1$H NMR (CDCl$_3$): δ2.89 (t, 2H); 3.95 (t, 2H); 4.65 (s, 2H); 6.97–7.14 (m, 3H). IR (neat): 2931, 2852, 2486, 1424, 1293, 1106 cm$^{-1}$.

RUN E

7-Fluoroisochroman (1e, 69% yield). $^1$H NMR (CDCl$_3$): δ2.85 (t, 2H); 3.98 (t, 2H); 4.75 (s, 2H); 6.76 (m, 1H); 6.95 (m, 1H); 7.23 (m, 1H). IR (neat): 2931, 2859, 1502, 1432, 1260, 1223, 1113, 1095, 949 cm$^{-1}$.

RUN F

Synthesis of 7-Iodoisochroman (1f; 51%):

A solution of 7-bromoisochroman (6.6 g; 30.98 mmol) in THF (100 ml) was cooled to −78° C. and treated with 2.1 eq of tert-butyllithium (40 ml of a 1.7M solution). After stirring the solution for one minute, iodine (8.64 g; 34.08 mmol) was added as a THF solution (50 ml). The reaction mixture was stirred for 30 minutes at −78° C. and one hour at room temperature. It was quenched with saturated aqueous ammonium chloride, and the organic phase was washed with aqueous sodium thiosulfate and brine, dried, and freed of solvent. The crude product was recrystallized from hexane to provide the pure 5-iodoisochroman as a white crystalline solid, mp= 54°–56° C. (4.1 g; 51%). $^1$H NMR (CDCl$_3$): δ2.79 (t, 2H); 3.94 (t, 2H); 4.70 (s, 2H); 6.85 (d, 1H); 7.32 (s, 1H); 7.46 (d, 1H). IR (nujol): 2931, 2852, 1550, 1252, 1190, 1105, 1005, 987 cm$^{-1}$.

RUN G

Synthesis of 5,7-Dimethylisochroman (1g):

A mixture of alcohol 10 (2.75 g; 18 mmol), MEM chloride (3.36 g; 27 mmol) and N,N-diisopropylethylamine (3.49 g; 27 mmol) in methylene chloride (20 ml) was stirred together for 2 hours. The reaction mixture was partitioned between 1N HCl and methylene chloride; the organic phase was washed with brine, dried (MgSO$_4$) and the solvent evaporated.

The crude acetal was dissolved in 20 ml of dry methylene chloride and added via dropping funnel to a stirred, cooled (0° C.) solution of titanium tetrachloride (17 mmol) in 85 ml of methylene chloride. After stirring at 0° C. for 2 hours the reaction was quenched by the successive addition of methanol (5 ml) and 1N HCl (100 ml). The layers were separated and the organic phase was washed with brine, dried (MgSO$_4$) and freed of solvent. The crude material was recrystallized from hexane to obtain 1.2 g (44%) of the isochroman. $^1$H NMR (CDCl$_3$): δ2.19, 2.27 (s, 3H each); 2.66 (t, 2H); 3.98 (t, 2H); 4.72 (s, 2H); 6.65 (s, 1H); 6.87 (s, 1H).

SCHEME II 2,4-Dimethylbenzyl alcohol (Compound 6):

A solution of 2,4-dimethylbenzoic acid (10 g; 66.6 mmol) in dry tetrahydrofuran (250 ml) was cooled to 0° C. and treated with a solution of diborane in tetrahydrofuran (135 ml of a 1.0M solution). The reaction mixture was stirred overnight before quenching with 1N HCl and extraction of the product into ethyl acetate. The organic phase was dried (MgSO$_4$) and freed of solvent. The crude product was filtered through a plug of silica, eluting with 10% ethyl acetate in hexane, to obtain 8.62 g (95%) of the alcohol as a clear oil. $^1$H NMR (CDCl$_3$): δ2.30, 2.32 (s, 6H total); 4.63 (d, 2H); 6.99 (m, 2H); 7.23 (d, 1H). IR (neat): 3338, 2921, 1504, 1453, 1378, 1240, 1039, 1005, 820 cm$^{-1}$.

2,4-Dimethylbenzyl bromide (Compound 7):

A solution of benzyl alcohol and compound 6 (18.4 g; 135 mmol) and carbon tetrabromide (55.96 g; 169 mmol) in methylene chloride (220 ml) was cooled to 0° C. and treated in dropwise fashion with triphenylphosphine (44.33 g; 169 mmol) in 100 ml of methylene chloride. After the addition was complete the mixture was stirred overnight at room temperature. It was poured into ice-water and partitioned between methylene chloride and water. The organic phase was dried (MgSO$_4$) and concentrated in vacuo. Chromatography of the residue, eluting with 10% ethyl. acetate in hexane, gave 26 g (99%) of the product as a yellow liquid. $^1$H NMR (CDCl$_3$): δ2.31, 2.38 (s, 3H each); 4.51 (s, 2H); 6.99 (m, 2H); 7.18 (d, 1H). IR (neat): 3013, 2972, 2921, 1617, 1507, 1450, 1262, 823 cm$^{-1}$.

2,4-Dimethylbenzyl cyanide (Compound 8):

A mixture of bromide compound 7 (25.9 g; 130 mmol) and sodium cyanide (7.97 g; 160 mmol) in DMSO (100 ml) was heated to 80° C. for 4 hours. After cooling, the reaction mixture was partitioned between water and ethyl acetate, and the organic phase was washed with brine, dried (MgSO$_4$) and concentrated in vacuo. Purification of the crude product on a silica gel column, eluting with 20% ethyl acetate in hexane, gave 13.8 g (73%) of the product as a brownish oil. $^1$H NMR (CDCl$_3$): δ2.24, 2.30 (s, 3H each); 3.61 (s, 2H); 7.03 (m, 2H); 7.23 (d, 1H). IR (neat): 2924, 2250, 1504, 1450, 1416, 1381, 1036, 820 cm$^{-1}$.

2,4-Dimethylphenylacetic acid (Compound 9):

A solution of nitrile compound 8 (13.8 g) was refluxed vigorously for 5 days in a mixture of ethanol (80 ml), water (40 ml) and potassium hydroxide (20 g). The ethanol was removed in vacuo and the residue was acidified with concentrated HCl to pH 1. The resulting white precipitate was collected via vacuum filtration, washed with cold water, and dried in a vacuum desiccator. The carboxylic acid was obtained as an off-white solid (14 g; 90%). $^1$H NMR (CDCl$_3$): δ2.25, 2.29 (s, 3H each); 3.62 (s, 2H); 6.98–7.01 (m, 3H). IR (nujol): 2921, 1710, 1550, 1412, 1247, 770 cm$^{-1}$.

2,4-Dimethylphenethyl alcohol (Compound 10):

A solution of carboxylic acid compound 9 (3.40 g; 17.87 mmol) in THF (100 ml) was cooled to 0° C. and treated with 35 ml of a 1.0M solution of borane in THF. After stirring this mixture overnight it was quenched with 1N HCl and the product was extracted into ethyl acetate. The ethyl acetate layer was washed with water, dried (MgSO4) and freed of solvent. The crude product was filtered through a plug of silica gel eluting with 20% ethyl acetate in hexane to obtain 2.75 g (quantitative yield) of the product as a clear light oil. $^1$H NMR (CDCl$_3$): δ2.25, 2.28 (s, 3H each); 2.88 (t, 2H); 3.78 (t, 2H); 6.97-7.07 (m, 3H). IR (neat): 3340, 2947, 1504, 1448, 1265, 1044 cm$^{-1}$.

PREPARATION II

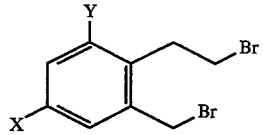

| Compounds | Run | Y Substituents | X Substituents |
|---|---|---|---|
| 2a | A | H | CH$_3$ |
| 2b | B | H | C$_2$H$_5$ |
| 2c | C | H | Br |
| 2d | D | H | Cl |
| 2e | E | H | F |
| 2f | F | H | I |
| 2g | G | CH$_3$ | CH$_3$ |
| 2h | H | H | NO$_2$ |

General Procedure for the Synthesis of 5-Substituted 2-(2-Bromoethyl) Benzyl Bromides of compound 2.

A solution of 7-substituted isochroman of compound 1 and 30% HBr in acetic acid (1 ml/4 mmol) was heated in a sealed tube at 100° C. for 16 hours. After cooling to room temperature, the reaction mixture was poured into ice water. The product was extracted into ether and the organic phase was washed with brine, dried (MgSO4) and freed of solvent. Chromatography of the residue on silica gel with 5% ethyl acetate-hexane furnished dibromide of compound 2.

RUN A 2-(2-Bromoethyl)-5-methylbenzyl bromide (2a, 89% yield). $^1$H NMR (CDCl$_3$): δ2.31 (s, 3H); 3.25 (t, 2H); 3.61 (t, 2H); 4.52 (s, 2H); 7.18 (m, 3H).

RUN B 2-(2-Bromoethyl)-5-ethylbenzyl bromide (2b, 92% yield). $^1$H NMR (CDCl$_3$): δ1.2 (t, 3H); 2.5 (q, 2H); 3.2 (m, 2H); 3.5 (m, 2H); 4.5 (s, 2H); 7.2 (m, 3H).

RUN C 2-(2-Bromoethyl)-5-bromobenzyl bromide (2c, 84% yield). $^1$H NMR (CDCl$_3$): δ3.24 (t, 2H); 3.61 (t, 2H); 4.47 (s, 2H); 7.08-7.50 (m, 3H). IR (nujol): 3010, 2350, 1590, 1480, 1260, 1225, 1090, 980 cm$^{-1}$. Mp=66°-69° C.

RUN D 2-(2-Bromoethyl)-5-chlorobenzyl bromide (2d, 92% yield). $^1$H NMR (CDCl$_3$): δ3.26 (t, 2H); 3.60 (t, 2H); 4.47 (s, 2H); 7.16 (d, 1H); 7.26 (dd, 1H); 7.34 (d, 1H).

RUN E 2-(2-Bromoethyl)-5-fluorobenzyl bromide (2e, 80% yield). $^1$H NMR (CDCl$_3$): δ3.26 (t, 2H); 3.61 (t, 2H); 4.49 (s, 2H); 6.97-7.26 (m,. 3H).

RUN F 2-(2-Bromoethyl)-5-iodobenzyl bromide (2f; 81% yield). $^1$H NMR (CDCl$_3$): δ3.24 (t, 2H); 3.63 (t, 2H); 4.45 (s, 2H); 6.96 (d, 1H); 7.63 (d, 1H); 7.69 (d, 1H).

RUN G 2-(2-Bromoethyl)-3,5-dimethylbenzyl bromide (2 g; 95% yield). $^1$H NMR (CDCl$_3$): δ2.27, 2.32 (s, 3H each); 3.28 (t, 2H); 3.58 (t, 2H); 4.53 (s, 2H); 6.97 (s, 1H); 7.02 (s, 1H).

RUN H

Synthesis of 5-nitro-2-(2-bromoethyl)benzyl bromide (2 h):

A mixture of dimesylate 12 (6 g; 17 mmol), lithium bromide (4.5 g; 51.8 mmol) and acetone (30 mL) is refluxed overnight under an inert atmosphere. After cooling to room temperature, the mixture is filtered and the solid is further washed with acetone. The combined organic washings are concentrated under reduced pressure to afford crude dibromide 13, which can be purified by column chromatography.

SCHEME III 2-(2-hydroxyethyl)-5-nitrobenzyl alcohol (Compound 11):

An ice-cooled solution of 5-nitrohomophthalic acid (3.0 g; 13.3 mmol) in tetrahydrofuran (25 mL) is treated with a 1M solution of diborane in tetrahydrofuran (50 mL; 50 mmol) in dropwise fashion and the resulting solution is stirred at room temperature. Upon completion of reaction as judged by tlc analysis, the mixture is quenched by the addition of water (25 mL) and the mixture is extracted with ethyl acetate (3×25 mL). The combined organic extracts are dried (MgSO4) and concentrated. Purification of the residue thus obtained by column chromatography affords diol 11 which can be recrystallized from chloroform.

2-(2-hydroxyethyl)-5-nitrobenzyl alcohol dimesylate (Compound 12):

To an ice-cooled solution of diol 11 (700 mg; 3.55 mmol), triethylamine (6.0 mL; 42.65 mmol) and chloroform (30 mL) is slowly added methanesulfonyl chloride (1.65 mL; 21.32 mmol). After stirring for 1 hour the ice bath is removed and stirring is continued for an additional 3 hours. Ice water (20 mL) is then added and the mixture is extracted with chloroform (3×25 mL). The organic extracts are dried (MgSO4) and concentrated under reduced pressure. Purification of the residual oil by column chromatography affords dimesylate 12.

PREPARATION III

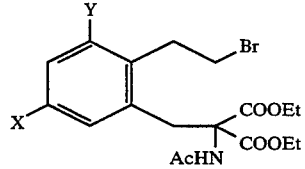

| Compounds | Run | Y Substituents | X Substituents |
|---|---|---|---|
| 3a | A | H | CH$_3$ |
| 3b | B | H | C$_2$H$_5$ |
| 3c | C | H | Br |
| 3d | D | H | Cl |
| 3e | E | H | F |
| 3f | F | H | I |

PREPARATION III

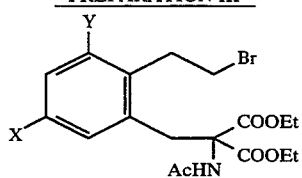

| Compounds | Run | Y Substituents | X Substituents |
|---|---|---|---|
| 3g | G | CH3 | CH3 |
| 3h | — | H | NO2 |

General Procedure for the Synthesis of Bromomalonates of compound 3:

To a cooled (10° C.) solution of tetrabutylammonium hydrogen sulfate (50 mmol) in 10% aqueous sodium hydroxide (2.5 equivalents of sodium hydroxide) was added methylene chloride (50 ml) followed by a solution of dibromide 2 (50 mmol) and diethylacetamidomalonate (55 mmol) in methylene chloride (50 ml). After stirring this mixture for 2 hours it was diluted with methylene chloride (200 ml), transferred to a separatory funnel, and the organic phase was washed several times with water and brine, dried (MgSO4) and freed of solvent. Purification by silica gel chromatography (30% ethyl acetate in hexane) afforded the bromomalonates.

RUN A

Ethyl 3-[(2-bromoethyl-5-methyl)phenyl]-2-carboethoxy-2-acetamidopropanoate (3a; 92% yield). $^1$H NMR (CDCl$_3$): δ1.30 (t, 6H); 2.01 (s, 3H); 2.26 (s, 3H); 3.04 (t, 2H); 3.44 (t, 2H); 3.66 (s, 2H); 4.27 (m, 4H); 6.56 (s, 1H); 6.79 (s, 1H); 7.04 (m, 2H). IR (CDCl$_3$): 1742, 1669 cm$^{-1}$.

RUN B

Ethyl 3-[(2-bromoethyl-5-ethyl)phenyl]-2-carboethoxy-2-acetamidopropanoate (3b; 90% yield). $^1$H NMR (CDCl$_3$): δ1.20 (t, 3H); 1.30 (t, 6H); 2.01 (s, 3H); 2.63 (q, 2H); 3.02 (t, 2H); 3.43 (t, 2H); 3.72 (s, 2H); 4.30 (m, 4H); 6.54 (s, 1H); 6.80–7.23 (m, 3H). IR (neat): 1743, 1668 cm$^{-1}$.

RUN C

Ethyl 3-[(2-bromoethyl-5-bromo)phenyl]-2-carboethoxy-2-acetamidopropanoate (3c; 72% yield). $^1$H NMR (CDCl$_3$): δ1.30 (m, 6H); 2.04 (s, 3H); 3.03 (dd, 2H); 3.43 (dd, 2H); 3.68 (s, 2H); 4.22–4.34 (m, 4H); 6.57 (br s, 1H); 7.04–7.35 (m, 3H). IR (nujol): 3296, 1748, 1645, 1519, 1308, 1277, 1221, 1190 cm$^{-1}$. Mp=102°–103° C.

RUN D

Ethyl 3-[(2-bromoethyl-5-chloro)phenyl]-2-carboethoxy-2-acetamidopropanoate (3d, 77% yield). $^1$H NMR (CDCl$_3$): δ1.27 (t, 6H); 2.03 (s, 3H); 2.98 (t, 2H); 3.58 (t, 2H); 3.69 (s, 2H); 4.21–4.30 (m, 4H); 6.62 (br s, 1H); 6.98 (s, 1H); 7.13–7.17 (m, 2H). IR (nujol): 3292, 2905, 1748, 1646, 1519, 1460, 1376, 1309, 1196, 1054, 1021 cm$^{-1}$.

RUN E

Ethyl 3-[(2-bromoethyl-5-fluoro)phenyl]-2-carboethoxy-2-acetamidopropanoate (3e, 84% yield). $^1$H NMR (CDCl$_3$): δ1.27 (t, 6H); 2.03 (s, 3H); 2.99 (t, 2H); 3.58 (t, 2H); 3.70 (t, 2H); 4.20–4.33 (m, 4H); 6.60 (br s, 1H); 6.73 (dd, 1H);. 6.94 (m, 1H); 7.15 (t, 1H). IR (CHCl$_3$): 3019, 1738, 1680, 1501, 1219 cm$^{-1}$.

RUN F

Ethyl 3-[(2-bromoethyl-5-iodo)phenyl]-2-carboethoxy-2-acetamidopropanoate (3f, 65%). $^1$H NMR (CDCl$_3$): δ1.31 (t, 6H); 2.04 (s, 3H); 3.03 (t, 2H); 3.44 (t, 2H); 3.65 (s, 2H); 4.32 (m, 4H); 6.56 (br s, 1H); 6.94 (d, 1H); 7.34 (s, 1H); 7.53 (dd, 1H). IR (CHCl$_3$): 3019, 1738, 1680, 1497, 1214 cm$^{-1}$.

RUN G

Ethyl 3-[(2-bromoethyl-3,5-dimethyl)phenyl]-2-carboethoxy-2-acetamidopropanoate (3 g, 73% yield). $^1$H NMR (CDCl$_3$): δ1.27 (t, 6H); 2.03 (s, 3H); 2.21, 2.28 (s, 3H each); 3.04 (t, 2H); 3.26 (t, 2H); 3.66 (s, 2H); 4.22 (q, 4H); 6.51 (s, 1H); 6.64 (s, 1H); 6.89 (s, 1H). IR (CDCl$_3$): 3415, 2983, 1738, 1680, 1494, 1280, 1203, 910, 728 cm$^{-1}$.

PREPARATION IV

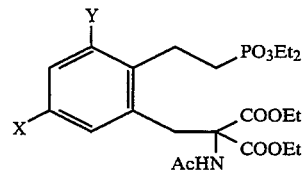

| Compounds | Run | Y Substituents | X Substituents |
|---|---|---|---|
| 4a | A | H | CH3 |
| 4b | B | H | C2H5 |
| 4c | C | H | Br |
| 4d | D | H | Cl |
| 4e | E | H | F |
| 4f | F | H | I |
| 4g | G | CH3 | CH3 |
| 4h | H | H | NO2 |
| 4i | I | H | NH2 |

General Procedure for the Synthesis of Diethylphosphonates of compound 4:

A solution of bromomalonate 3 (10 mmol) in triethylphosphite (50–100 ml) was refluxed overnight. The excess triethylphosphite was removed through distillation and the residue was purified in a silica gel column, eluting with first ethyl acetate and then 10% methanol in ethyl acetate, to give compound 4 as a viscous oil.

RUN A

Ethyl 3-[(2-{diethoxyphosphinyl}ethyl-5-methyl)-phenyl]-2-carboethoxy-2-acetamidopropanoate (4a, 80% yield). $^1$H NMR (CDCl$_3$): δ1.32 (m, 12H); 1.95 (m, 2H); 2.02 (s, 3H); 2.26 (s, 3H); 2.78 (m, 2H); 3.65 (s, 2H); 4.10 (m, 4H); 4.26 (m, 4H); 6.58 (s, 1H); 6.78 (s, 1H); 7.04 (m, 2H). IR (neat): 1746, 1671 cm$^{-1}$.

RUN B

Ethyl 3-[(2-{diethoxyphosphinyl}ethyl-5-ethyl)-phenyl]-2-carboethoxy-2-acetamidopropanoate (4b, 75% yield). $^1$H NMR (CDCl$_3$): δ1.10–1.42 (m, 15H); 1.89–2.02 (m, 2H); 2.10 (s, 3H); 2.51–2.63 (q, 2H); 2.68–2.91 (q, 2H); 3.74 (s, 2H); 3.98–4.23 (m, 4H); 4.24–4.45 (m, 4H); 6.80 (s, 1H); 6.84–7.33 (m, 3H). IR (neat): 1745, 1676 cm$^{-1}$.

RUN C

Ethyl 3-[(2-{diethoxyphosphinyl}ethyl-5-bromo)-phenyl]-2-carboethoxy-2-acetamidopropanoate (4c, 99% yield). $^1$H NMR (CDCl$_3$): δ1.10–1.37 (m, 12H); 1.85–1.97 (m, 2H); 2.05 (s, 3H); 2.78 (m, 2H); 3.66 (s, 2H); 4.05–4.32 (m, 8H); 6.62 (s, 1H); 7.04–7.33 (m, 3H). IR (neat): 3225, 2980, 1740, 1675, 1480, 1250, 1050 cm$^{-1}$.

RUN D

Ethyl 3-[(2-{diethoxyphosphinyl}ethyl-5-chloro)-phenyl]-2-carboethoxy-2-acetamidopropanoate (4d, 42% yield). $^1$H NMR (CDCl$_3$): δ1.11–1.35 (m, 12H); 1.83–1.96 (m, 2H); 2.04 (s, 3H); 2.82 (m, 2H); 3.66 (s, 2H); 4.07 (m, 4H); 4.25 (m, 4H); 6.58 ( s, 1H). IR (CHCl$_3$): 3021, 1741, 1680, 1500, 1233, 1021 cm$^{-1}$.

RUN E

Ethyl 3-[(2-{diethoxyphosphinyl}ethyl-5-fluoro)-phenyl]-2-carboethoxy-2-acetamidopropanoate (4e, 60% yield). $^1$H NMR (CDCl$_3$): δ1.11–1.19 (m, 12H); 1.85–1.98 (m, 2H); 2.03 (s, 3H); 2.81 (m, 2H); 3.65 (s, 2H); 3.99–4.37 (m, 8H); 6.61 (s, 1H); 6.72 (dd, 1H); 6.88 (m, 1H); 7.17 (m, 1H). IR (CHCl$_3$): 3019, 1738, 1679, 1501, 1216, 1023, 753 cm$^{-1}$.

RUN F

Ethyl 3-[(2-{diethoxyphosphinyl}ethyl-5-iodo)-phenyl]-2-carboethoxy-2-acetamidopropanoate (4f, 85% yield). $^1$H NMR (CDCl$_3$): δ1.07–1.35 (m, 12H); 1.67–1.96 (m, 2H); 2.06 (s, 3H); 2.76 (m, 2H); 3.63 (s, 2H); 3.99–4.18 (m, 4H); 4.21–4.33 (m, 4H); 6.57 (s, 1H); 6.93 (d, 1H); 7.32 (s, 1H); 7.51 (d, 1H). IR (nujol): 3247, 2980, 1743, 1674, 512, 1481, 1391, 1370, 1221, 1033, 962 cm$^{-1}$.

RUN G

Ethyl 3-[(2-{diethoxyphosphinyl}ethyl-3,5-dimethyl)phenyl]-2-carboethoxy-2-acetamidopropanoate (4 g, 65% yield). $^1$H NMR (CDCl$_3$): δ1.19–1.37 (m, 12H); 1.72–1.82 (m, 2H); 2.03 (s, 3H); 2.21, 2.28 (s, 3H each); 2.78 (m, 2H); 3.63 (s, 2H); 4.06–4.38 (m, 8H); 6.52 (s, 1H); 6.63 (s, 1H); 6.87 (s, 1H).

RUN H

Ethyl 3-[(2-{diethoxyphosphinyl}ethyl-5-nitro)-phenyl]-2-carboethoxy-2-acetamido propanoate (4 h). $^1$H NMR (CDCl$_3$) δ1.2–1.4 (m, 12H), 1.9–2.1 (m, 5H); 2.8–3.0 (m, 2H), 3.81 (s, 2H), 4.0–4.2 (m, 4H), 4.2–4.4 (m, 4H), 6.60 (s, 1H), 7.18 (d, 1H, J=8.46 Hz), 7.97 (dd, 1H, J=2.33, 8.53 Hz), 8.07 (d, 1H, J=2.36 Hz).

RUN I

Ethyl 3-[(2-{diethoxyphosphinyl}ethyl-5-methyl)-phenyl]-2-carboethoxy-2-acetamido propanoate (4i).

A solution of nitro compound 4 h (2 mmol), concentrated HCl (1 mL) and ethanol (50 mL) is hydrogenated over 10% Pd/C (100 mg) at a pressure of 3 atmospheres. After 2 hours, the mixture is filtered through a pad of celite and concentrated to afford the hydrochloride salt of 4i. This salt is partitioned between saturated NaHCO$_3$ (20 mL) and ethyl acetate, (20 mL) and the aqueous layer is further extracted with ethyl acetate (2×20 mL). The combined organic layers are dried (K$_2$CO$_3$) and concentrated. Purification of the resulting residue by column chromatography affords 4i.

PREPARATION V

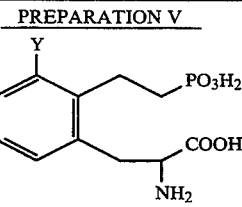

| Example | Compounds | Run | Y Substituents | X Substituents |
|---|---|---|---|---|
| I | 5a | A | H | CH$_3$ |
| II | 5b | B | H | C$_2$H$_5$ |
| III | 5c | C | H | Br |
| IV | 5d | D | H | Cl |
| V | 5e | E | H | F |
| VI | 5f | F | H | I |
| VII | 5g | G | CH$_3$ | CH$_3$ |
| VIII | 5h | — | H | NO$_2$ |
| IX | 5i | — | H | NH$_2$ |

General Procedure for the Preparation of Phosphonoethyl phenylalanines of compound 5.

A solution of tetraester compound 4 (10 mmol) in 6N HCl (100 ml) was refluxed overnight. Evaporation of the solvent furnished the hydrochlorides of compound 5, which were washed with acetone. Free amino acids of compound 5 were obtained by addition of propylene oxide to a solution of compound 5 (hydrochloride salt) in ethanol. Crude product of compound 5 was washed with acetone and ethanol, and then dried under vacuum.

RUN A

5-Methyl-2-(2-phosphonoethyl)phenylalanine (5a, 96% yield). $^1$H NMR (D$_2$O): δ1.40 (m, 3H); 2.06 (s, 3H); 2.35 (m, 3H); 2.82 (dd, 1H); 3.25 (t, 1H); 6.87 (d, 2H); 7.01 (d, 1H). IR (KBr): 3132, 2936, 1712, 1627, 1548, 1067, 933 cm$^{-1}$. Mp >230° C. (dec). Anal. Calcd. for C$_{12}$H$_{18}$NO$_5$P: C, 50.18; H, 6.32; N, 4.88. Found: C, 50.07; H, 6.35; N, 4.85.

RUN B

5-Ethyl-2-(2-phosphonoethyl)phenylalanine (5b, 95% yield). $^1$H NMR (D$_2$O); δ1.15 (t, 3H); 1.69–1.93 (m, 2H); 2.42–2.58 (q, 2H); 2.60–2.81 (m, 2H); 3.23 (dd, 2H); 3.40 (t, 1H); 6.98–7.20 (m, 3H). IR (nujol): 1722 cm$^{-1}$. Mp>205° C. Anal. Calcd. for C$_{13}$H$_{20}$NO$_5$P-Cl.0.5H$_2$O: C, 50.32; H, 6.82; N, 4.51. Found: C, 50.09; H, 6.51; N, 4.49.

RUN C

5-Bromo-2-(2-phosphonoethyl)phenylalanine (5c, 52% yield). $^1$H NMR (D$_2$O): δ1.47–1.58 (m, 2H); 2.59–2.67 (m, 2H); 2.91–3.06 (m, 2H); 3.68–3.73 (s, 1H); 7.05–7.27 (m, 3H). IR (KBr): 2935, 1600, 1400, 1220, 1135, 1040, 900 cm$^{-1}$. Anal. Calcd. for C$_{11}$H$_{15}$NO$_5$BrP: C, 37.52; H, 4.29; N, 3.98; Br, 22.69. Found: C, 37.44; H, 3.92; Br, 22.59.

RUN D

5-Chloro-2-(2-phosphonoethyl)phenylalanine (5d, 46% yield). $^1$H NMR (D$_2$O): d 1.42 (m, 2H); 2.63 (m, 3H); 2.82 (dd, 1H); 3.28 (t, 1H); 7.05 (m, 3H). IR (KBr): 2931, 1725, 1596, 1486 cm$^{-1}$. Mp>160° C. Anal. Calcd. for C$_{11}$H$_{15}$NO$_5$PCl.0.5H$_2$O. C, 41.72; H, 5.09; N, 4.42. Found: C, 41.98; H, 4.84; N, 4.38.

RUN E

5-Fluoro-2-(2-phosphonoethyl)phenylalanine (5e, 75% yield). $^1$H NMR (D$_2$O): δ1.75 (m, 2H); 2.72 (m, 2H); 3.08 (m, 1H); 3.20 (m, 1H); 4.04 (t, 1H); 6.92 (m, 2H); 7.22 (m, 1H). IR (nujol): 2913, 1725, 1618, 1515, 1365, 1046, 953 cm$^{-1}$. Mp>220° C. Anal. Calcd. for C$_{11}$H$_{15}$NO$_5$PF.0.5 H$_2$O: C, 43.74; H, 5.41; N, 4.64. Found: C, 43.81; H, 5.51; N, 4.58.

RUN F

5-Iodo-2-(2-phosphonoethyl)phenylalanine (5f, 58% yield). $^1$H NMR (D$_2$O): δ1.34–1.48 (m, 2H); 2.54–2.85 (m, 4H); 3.26 (t, 1H); 6.92 (d, 1H); 7.41 (m, 2H). IR (nujol): 2910, 1722, 1620, 1525, 1460, 1378, 1044, 951 cm$^{-1}$. Mp>190° C. Anal. Calcd. for C$_{11}$H$_{15}$NO$_5$P.0.5-H$_2$O: C, 32.37; H, 3.95; N, 3.43. Found: C, 32.71; H, 4.10; N, 3.20.

RUN G 3,5-Dimethyl-2-(2-phosphonoethyl)phenylalanine (5 g, 40% yield). $^1$H NMR (D$_2$O): d 1.27 (m, 2H); 2.06 (s, 3H); 2.14 (s, 3H); 2.64 (m, 3H); 2.83 (dd, 1H); 3.28 (t, 1H); 6.74 (s, 1H); 6.80 (s, 1H). IR (nujol): 2897, 1725, 1612, 1460, 1378, 1044 cm$^{-1}$. Mp>235° C. Anal. Calcd. for C$_{13}$H$_{20}$NO$_5$P.0.5H$_2$O: C, 50.32; H, 6.82; N, 4.51. Found: C, 50.54; H, 6.61; N, 4.37.

EXAMPLE X

The general procedure for the preparation of phosphonoethyl phenylalanines was used to prepare the compound of Example X, 5-t-Butyl-2-(2-phosphonoethyl)phenylalanine. The preparation provided 91% yield: mp 216°–217° C.; $^1$H NMR (D$_2$O/NaOD) δ1.12 (s, 9H), 1.32 (m, 2H), 2.80 (m, 3H), 3.34 (t, 1H), 7.16 ppm (m, 3H); IR (KBr) 1718 cm$^{-1}$. Anal. Calcd. for C$_{15}$H$_{24}$NO$_5$P.0.44 H$_2$O: C, 53.42; H, 7.44; N, 4.15. Found: C, 53.44; H, 7.50; N, 4.15.

EXAMPLE XI

The general procedure for the preparation of phosphonoethyl phenylalanines was used to prepare the compound of Example XI, 5-Phenyl-2-(2phosphonoethyl)-phenylalanine. The preparation provided 82% yield: mp 245° C. (decomp.); $^1$H NMR (D$_2$O) δ1.3–1.5 (m, 2H), 2.5–2.7 (m, 3H), 2.9 (m, 1H), 3.3 (m, 1H), 7.0–7.6 ppm (m, 8H); IR (nujol) 1712 cm$^{-1}$. Anal. Calcd. for C$_{17}$H$_{20}$NO$_5$P.0.33 H$_2$O: C, 57.46; H, 5.86; N, 3.94. Found: C, 57.66; H, 5,87; N, 3.95.

EXAMPLE XII

The general procedure for the preparation of phosphonoethyl phenylalanines was used to prepare the compound of Example XII, 5-Cyclohexyl-2-(2-phosphonoethyl) phenylalanine hydrochloride. The preparation provided a 62% yield: mp 216°–218° C.; $^1$H NMR (D$_2$O) δ0.9–1.8 (m, 12H), 2.3 (bs, 1H), 2.6 (m, 3H), 2.8 (m, 1H), 3.3 (m, 1H), 6.8–7.2 ppm (m, 3H); IR (nujol) 1717 cm$^{-1}$. Anal. Calcd. for C$_{17}$H$_{26}$NO$_5$P.HCl.H$_2$O: C, 50.29; H, 7.12; N, 3.44; Cl, 8.82. Found: C, 49.82; H, 7.13, H, 3.41; Cl, 8.65.

EXAMPLE XIII

The general procedure for the preparation of phosphonoethyl phenylalanines was used to prepare the compound of Example XIII, 5-Octyl-2-(2-phosphonoethyl)phenylalanine hydrochloride. The preparation provided a 95% yield: mp 228°–230° C.; $^1$H NMR (D$_2$O/NaOD) δ0.67 (t, 3H), 1.12 (m, 10H), 1.43 (m, 4H), 2.37 (t, 2H), 2.59 (m, 3H), 2.92 (dd, 1H), 3.27 (dd, 1H), 6.90 (d, 2H), 7.06 ppm (d, 1H); IR (KBr) 1720 cm$^{-1}$. Anal. Calcd. for C$_{19}$H$_{32}$NO$_5$P.HCl: C, 54.09; H, 7.88; N, 3.32; Cl, 8.40. Found: C, 54.08; H, 7.91; N, 3.31; Cl, 8.47.

EXAMPLE XIV

The general procedure for the preparation of phosphonoethyl phenylalanines was used to prepare the compound of Example XIV, 5-Pentadecyl-2-(2-phosphonoethyl) phenylalanine hydrochloride. The preparation provided a 78% yield: mp 211°–214° C.; $^1$H NMR (D$_2$O/NaOD) δ0.81 (m, 3H), 1.30 (m, 24H), 1.53 (m, 4H), 2.35 (m, 3H), 2.67 (m, 2H), 3.07 (m, 1H), 3.25 (m, 1H), 6.80 (m, 2H), 7.09 ppm (m, 1H); IR (KBr) 1702 cm$^{-1}$. Anal. Calcd. for C$_{26}$H$_{47}$NO$_5$P.HCl: C, 59.92; H, 9.28; N, 2.68; Cl, 6.80. Found: C, 60.09; H, 9.21; N, 2.60; Cl, 6.50.

EXAMPLE XV

The general procedure for the preparation of phosphonoethyl phenylalanines was used to prepare the compound of Example XV, 3-Methyl-2-(2-phosphonoethyl)phenylalanine. The preparation provided a 70% yield: mp 253°–255° C. (decomp); $^1$H NMR (D$_2$O) δ1.60 (m, 2H), 2.20 (s, 3H), 2.75 (m, 2H), 3.09 (m, 2H), 3.89 (t, 1H), 7.02 ppm (n, 3H); IR (KBr) 1712 cm$^{-1}$. Anal. Calcd. for C$_{12}$H$_{18}$NO$_3$P.0.33 H$_2$O: C, 49.15; H, 6.42; N, 4.77. Found: C, 49.13; H, 6.45; N, 4.65.

EXAMPLE XVI

The general procedure for the preparation of phosphonoethyl phenylalanines was used to prepare the compound of Example XVI, 3-Phenyl-2-(2-phosphonoethyl) phenylalanine hydrochloride. The preparation provided a 93% yield: mp 220° C. (decomp); $^1$H NMR (D$_2$O) δ1.0–1.3 (m, 2H), 2.5–2.7 (m, 2H), 2.8 (m, 2H), 3.3 (t, 1H), 6.8–7.4 ppm (m, 9H); IR (nujol) 1717 cm$^{-1}$. Anal. Calcd. for C$_{17}$H$_{20}$NO$_5$P.HCl: C, 52.92; H, 5.48; N, 3.63; Cl, 9.19. Found: C, 52.83; H, 5.49; N, 3.59; Cl, 9.27.

PREPARATION VI

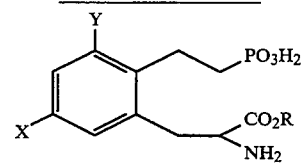

| EXAMPLE | Y SUBSTITUENT | X SUBSTITUENT | R |
|---|---|---|---|
| XVII | H | CH$_3$ | CH$_2$CH$_3$ |
| XVIII | H | C(CH$_3$)$_3$ | CH$_2$CH$_3$ |

A solution of amino acid compound 5 (8.5 mmol), excess ethereal hydrogen chloride (50 mL, 1.0M solution) and the appropriate alcohol (50 mL) was heated at reflux for 18 hours. The solvent was evaporated and the free amino ester was precipitated by the addition of propylene oxide to a solution of the hydrochloride salt in ethanol. The resultant product was washed successively with ethanol and ether and then dried under vacuum.

In the case of 4,5-disubstituted compounds, an alternative strategy is employed as exemplified by 2-(2-phosphonoethyl)-4,5-dichlorophenyl alanine (Scheme IV).

EXAMPLE XVII

The general procedure for the preparation of phosphonoethyl phenylalanine carboxylic esters was used to prepare the compound of Example XVII, 5-Methyl-2-(2-phosphonoethyl)phenylalanine ethyl ester. The preparation provided a 98% yield; mp 225°–227° C.; $^1$H NMR ($D_2O$) $\delta 0.94$ (t, 3H), 1.61 (m, 2H), 2.07 (s, 3H), 2.58 (m, 2H), 3.05 (d, 2H), 3.98 (q, 2H), 4.08 (t, 1H), 6.83 (s, 1H), 6.96 (d, 1H), 7.04 ppm (d, 1H); IR (KBr) 1748 cm$^{-1}$. Anal. Calcd. for $C_{14}H_{22}NO_5P \cdot 0.25H_2O$: C, 52.58; H, 7.09; N, 4.37. Found: C, 52.58; H, 7.12; N, 4.36.

EXAMPLE XVIII

The general procedure for the preparation of phosphonoethyl phenylalanine carboxylic esters was used to prepare the compound of Example XVIII, 5-t-Butyl-2-(2-phosphonoethyl)phenylalanine ethyl ester. The preparation provided a 88% yield; mp 213°–216° C.; $^1$H NMR ($D_2O$/NaOD) $\delta 0.48$ (t, 3H), 0.71 (m, 9H), 1.46 (m, 2H), 2.37 (m, 2H), 2.80 (m, 2H), 3.56 (m, 2H), 3.79 (m, 1H), 6.66 ppm (m, 3H); IR (KBr) 1749 cm$^{-1}$.

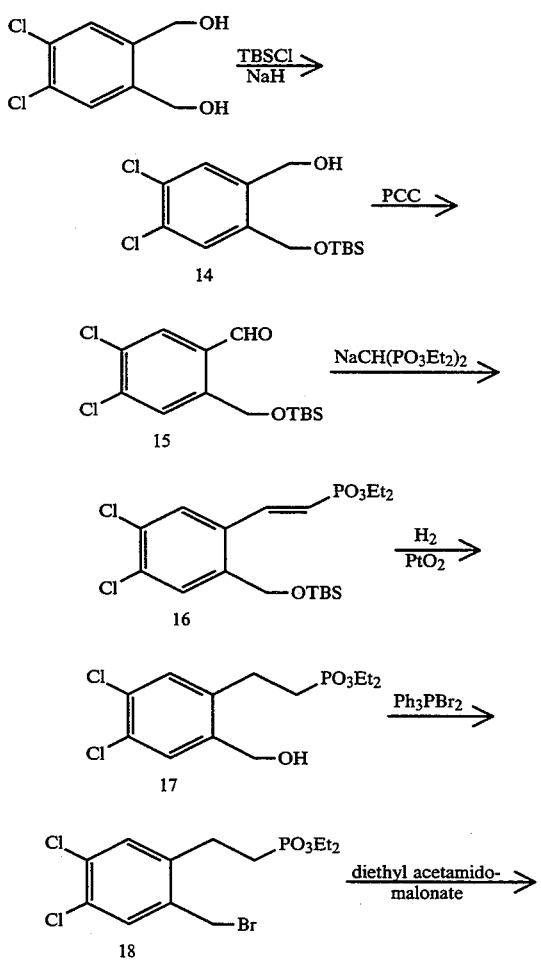

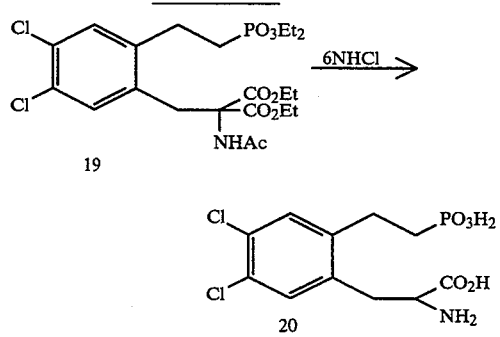

EXAMPLE XIX

Synthesis of 2-(2-phosphonoethyl)-4,5-dichlorophenylalanine (Compound 21):

A solution of tetraester 20 (10 mmol) in 6N HCl (100 mL) is refluxed for 24 hours. Evaporation of the solvent furnishes the hydrochloride salt of 21 which is washed with acetone. Liberation of the free amino acid of Compound 21 is accomplished by addition of propylene oxide to a solution of Compound 21 (hydrochloride salt) in ethanol. The product 21 thus obtained is washed with ethanol and acetone and dried under vacuum.

2-tert-butyldimethysilyloxymethyl-4,5-dichlorobenzyl alcohol (Compound 14):

To an ice-cooled suspension of sodium hydride (42.7 mmol) in dry tetrahydrofuran (300 mL) is added a solution of 4,5-dichlorobenzene-1,2-dimethanol [L. A. Levy, Syn. Commun. 13, 639–648 (1983)] (7.37 g; 35.6 mmol) in tetrahydrofuran (100 mL) in a dropwise fashion. The mixture is then allowed to stir at room temperature for 2 hours, after which time tert-butyldimethylsilyl chloride (5.37 g; 35.6 mmol) is added. After stirring for an additional 2 hours, the reaction mixture is poured into ether (600 mL), washed with 10% aqueous $K_2CO_3$ (1×300 mL) and brine (1×300 mL), dried (MgSO$_4$) and concentrated under reduced pressure. Purification of the resulting residual oil by column chromatography using ethyl acetate/hexane mixtures as eluent affords monosilyl ether 14.

2-tert-butyldimethylsilyloxymethyl-4,5-dichlorobenzaldehyde (Compound 15):

To a vigorously stirred mixture of alcohol 14 (5.77 g; 18.0 mmol) and powdered molecular sieves (8 g; 4 Å) in dry methylene chloride (90 mL) is added pyridinium chlorochromate (7.76 g; 36.0 mmol). After 1 hour, ether (200 mL) is added and the solution is decanted onto a column of Florisil. The solid inorganic salts are washed with ether (3×100 mL) and the washings are also passed through the Florisil column, which is then thoroughly washed with ether. Concentration of the combined ether washings affords the crude aldehyde 15 which is purified by column chromatography eluting with hexane.

2-(2-E-diethylphosphonoethenyl)-4,5-dichlorobenzyl alcohol, tert-butyldimethyl-silyl ether (Compound 16):

To an ice-cooled suspension of sodium hydride (2–3 mmol) in 1,2-dimethoxyethane (10 mL) is slowly added tetraethylmethylene diphosphonate (2.1 mmol). After stirring for 15 minutes, a solution of aldehyde 15 (2.1 mmol) in 1,2-dimethoxyethane (5 mL) is added and the resulting mixture is allowed to stir at room temperature.

Occasional warming of the mixture is required to facilitate stirring which is hampered by the oily precipitate. After 1 hour, water (20 mL) is added to quench the reaction and the mixture is extracted with ethyl acetate (3×25 mL). The combined organic extracts are dried (MgSO₄) and concentrated under reduced pressure. Purification of the residual oil by column chromatography (hexane/ethyl acetate mixtures) affords vinyl phosphonate 16.

2-(2-diethylphosphonoethenyl)-4,5-dichlorobenzyl alcohol (Compound 17):

A solution of vinyl phosphonate 16 (1 mmol) in ethanol (25 mL) is hydrogenated over platinum oxide (50 mg) at atmospheric pressure. After 24 hours, the mixture is filtered through a pad of celite and concentrated. Purification of the residual oil by column chromatography (hexane/ethyl acetate mixtures) affords the desilylated diethylphosphonate 17.

2-(2-diethylphosphonoethyl)-4,5-dichlorobenzyl bromide (Compound 18):

To a stirred solution of benzyl alcohol 17 (2 mmol) in dichloromethane (10 mL) is added dibromotriphenylphosphorane (2.2 mmol). After stirring for 1 hour, the mixture is poured onto a column of Florisil which is eluted with dichloromethane followed by a mixture of dichloromethane/methanol (100:1). Concentration of the Florisil washings affords crude bromide 18 which is purified by column chromatography.

Ethyl 3-[(2-{diethoxyphosphinyl}ethyl-4,5-dichloro)-phenyl]-2-carboethoxy-2-acetamidopropanoate (Compound 19):

To an ice-cooled solution of tetrabutylammonium hydrogen sulfate (5 mmol) in 10% aqueous sodium hydroxide (12.5 mmol) is added dichloromethane (5 mL) followed by a solution of benzyl bromide 18 (5.0 mmol) and diethyl acetamidomalonate (5.5 mmol) in dichloromethane (5 mL). After stirring this mixture for 2 hours, the mixture is diluted with dichloromethane (20 mL) and the organic phase is washed several times with water and brine, dried (MgSO₄) and concentrated. Purification by column chromatography (ethyl acetate/methanol mixtures) provides Compound 19.

In the case of the phosphonopropyl compounds (m=3), an alternative strategy is used, as exemplified by 5-methyl-2-(3-phosphonopropyl)phenylalanine (Scheme V).

SCHEME V

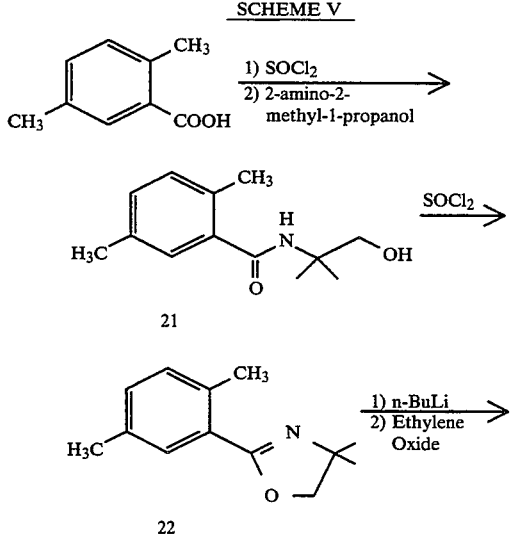

-continued
SCHEME V

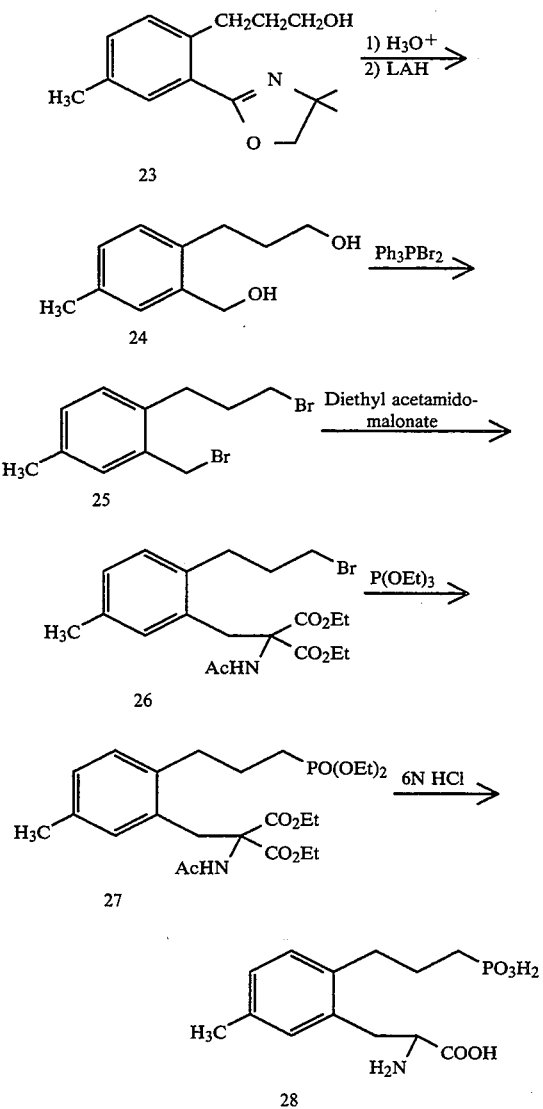

EXAMPLE XX

Synthesis of 5-methyl-2-(3-phosphonopropyl)-phenylalanine (Compound 28):

A solution of tetraester 27 (1.75 g) and 10N HCl (30 ml) was refluxed vigorously overnight. Evaporation of the solvent furnished the hydrochloride salt of 29, which was washed with acetone. Liberation of the free amino acid of Compound 29 was accomplished by the addition of propylene oxide to a solution of Compound 29 (hydrochloride salt) in ethanol. The product 29 thus obtained was washed with acetone and ethanol and dried under vacuum to obtain 460 mg of an amorphous white solid, mp>110° C. $^1$H NMR (D₂O): δ1.45 (m, 2H); 1.78 (m, 2H); 2.29 (s, 3H); 2.66 (m, 2H); 2.81 (m, 1H); 3.05 (m, 1H); 3.46 (t, 1H); 7.11 (m, 2H); 7.24 (m, 1H). IR (KBr): 2903, 1725, 1615, 1460, 1378, 1108, 1023 933 cm$^{-1}$. Anal. Calcd. C₁₃H₂₀NO₅P.0.5 H₂O: C, 50.32; H, 6.82; N, 4.51 Found: C, 50.26; H, 6.84; N, 4.40. N-(2-Methyl-3-hydroxyprop-2-yl)-2,5-dimethylbenzamide (Compound 21):

A mixture of 2,5-dimethylbenzoic acid (10 g; 66.59 mmol) and thionyl chloride (50 ml) was refluxed for 3 hours. Excess thionyl chloride was removed in vacuo to furnish 11.4 g of the acid chloride. This crude product was dissolved in methylene chloride (50 ml) and added in a dropwise fashion to a cooled (10° C.) solution of 2-amino-2-methyl-1-propanol (12.1 g; 135 mmol) in methylene chloride (50 ml). After stirring the mixture for one hour it was filtered through Celite and concentrated in vacuo to obtain 13.6 g (92%) of the product as a waxy semi-solid. $^1$H NMR (CDCl$_3$): δ1.30 (s, 6H); 2.28 (d, 6H); 3.64 (s, 2H); 4.69 (br, 1H); 6.02 (br, 1H); 7.12 (m, 3H).

2-(2,5-dimethylphenyl)-4,4-dimethyl-2-oxazoline (Compound 22):

Thionyl chloride, 30 ml, was added slowly to amide 21 (13.6 g; 61.5 mmol) in a round bottom flask, with stirring. After the addition was complete, the mixture was stirred for one hour and then concentrated. The crude residue was purified on a silica gel column, eluting with 10% ethyl acetate in hexane, to obtain 10.6 g (85%) of the oxazoline as a white solid. $^1$H NMR (CDCl$_3$): δ1.37 (s, 6H); 2.31 (s, 3H); 2.49 (s, 3H); 4.06 (s, 2H); 7.11 (m, 2H); 7.57 (m, 1H).

2-[2-(3-hydroxypropyl)-5-methylphenyl]-4,4-dimethyl-2-oxazoline (Compound 23):

A solution of oxazoline 22 (8.4 g; 41.4 mmol) in tetrahydrofuran (100 ml) was cooled to 0° C. and treated with n-butyllithium (18.2 ml of a 2.5M solution; 45.52 mmol). The red anion soluton was stirred at 0° C. for one hour, at which time ethylene oxide was added as an ethereal solution (100 ml of a 1.4M solution; 0.140 mol). The yellowish reaction mixture was stirred overnight at room temperature and then quenched by the addition of saturated aqueous ammonium chloride (100 ml). The product was partitioned between ethyl acetate and brine; the organic phase was washed with water, dried (MgSO$_4$) and freed of solvent. Purification of the crude material on a silica gel column, eluting with 50% ethyl acetate on hexane, delivered 10 g (98%) of Compound 23. $^1$H NMR (CDCl$_3$): d 1.44 (s, 6H); 1.90 (m, 2H); 2.34 (s, 3H); 3.07 (t, 2H); 3.43 (t, 2H); 4.13 (s, 2H); 7.27 (m, 2H); 7.58 (s, 1H).

2-(3-hydroxypropyl)-5-methylbenzyl alcohol (Compound 24):

Oxazoline 23 (10 g; 40.43 mmol) in 200 ml of 3N HCl was refluxed vigorously for 2.5 hours. The reaction mixture was cooled and partitioned between methylene chloride and water. The organic phase was washed several times with brine, dried (MgSO$_4$) and freed of solvent. The crude material was dissolved in anhydrous ether (150 ml) and added in a dropwise fashion to a solution of lithium aluminum hydride (55 mmol) in ether (100 ml). After stirring this mixture for 2.5 hours, water (100 ml) was added slowly and cautiously, followed by 100 ml of 1N HCl. After stirring for 30 minutes the mixture was homogeneous; it was extracted into ethyl acetate, dried (MgSO$_4$) and concentrated. The product was obtained as a thick oil (9.0 g). $^1$H NMR (CDCl$_3$): δ1.87 (m, 2H); 2.31 (s, 3H); 2.81 (1, 2H); 3.53 (t, 2H); 3.57 (s, 3H); 4.62 (s, 2H); 7.12 (m, 3H).

2-(3-bromopropyl)-5-methylbenzyl bromide (Compound 25):

Dibromotriphenylphosphorane (12.66 g; 30 mmol) was added as a methylene chloride solution (100 ml) to a solution of diol 24 (1.80 g; 9.99 mmol) in methylene chloride (50 ml). This mixture was stirred for 3 hours at room temperature and then partitioned between brine and methylene chloride. The layers were separated and the organic phase was dried (MgSO$_4$) and freed of solvent. The crude residue was purified on a silica gel column, eluting with 5% ethyl acetate in hexane, to obtain 1.5 g of Compound 25. $^1$H NMR (CDCl$_3$): δ2.20 (m, 2H); 2.28 (s, 3H); 2.86 (t, 2H); 3.46 (t, 2H); 4.53 (s, 2H); 7.16 (m, 3H).

Ethyl 3-[(2-(3-bromopropyl)-5-methyl)phenyl]-2-carboethoxy-2-acetamidopropanoate (Compound 26):

A mixture of dibromide 25 (1.5 g; 4.90 mmol), diethyl acetamidomalonate (1.3 g; 5.88 mmol) and tetrabutylammonium hydrogen sulfate (2.03 g; 5.88 mmol) was stirred in a two phase solvent mixture consisting of methylene chloride (20 ml) and 10% aqueous sodium hydroxide (10 ml). After 18 hours the mixture was washed with water (3×20 ml), dried (MgSO$_4$) and concentrated. The crude material was purified on a silica gel column, eluting with 40% ethyl acetate in hexane, to obtain 2.0 g (92%) of Compound 26 as a white solid. $^1$H NMR (CDCl$_3$): δ1.28 (m, 6H); 1.95 m, 2H); 2.01 (s, 3H); 2.25 (s, 3H); 2.65 (m, 2H); 3.48 (t, 2H); 3.65 (s, 2H); 4.28 (m, 4H); 6.54 (br, 1H); 6.76 (s, 1H); 7.07 (m, 2H).

Ethyl 3-[(2-{3-(diethoxyphosphinyl)propyl}-5-methyl)phenyl]-2-carboethoxy-2-acetamidopropanoate (Compound 27):

A mixture of bromide 26 (1.9 g; 4.29 mmol) and triethyl phosphite (50 ml) was refluxed vigorously overnight. After removal of the excess triethyl phosphite in vacuo, the residue was purified chromatographically (10% methanol in ethyl acetate) to obtain 1.77 g of Compound 27. $^1$H NMR (CDCl$_3$): δ1.33 (m, 12H); 1.77 (m, 4H); 2.01 (s, 3H); 2.23 (s, 3H); 2.58 (s, 2H); 3.63 (s, 2H); 4.22 (m, 8H); 6.51 (br, 1H); 6.78 (s, 1H); 7.02 (m, 2H).

In the case of the 5-trifluoromethyl compound, the following synthetic scheme is utilized (Scheme VI).

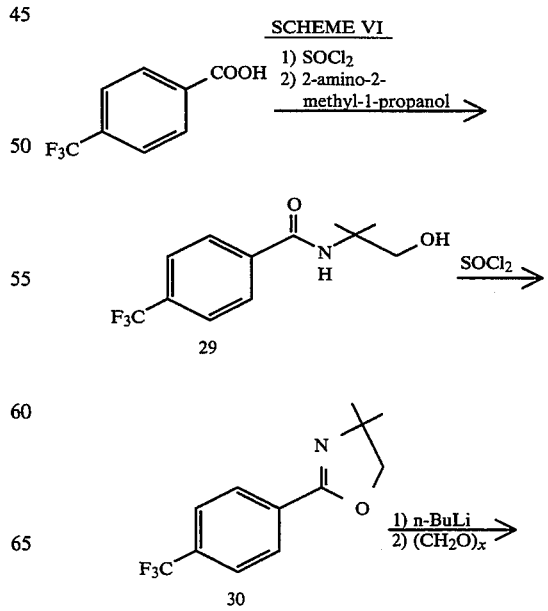

-continued
SCHEME VI

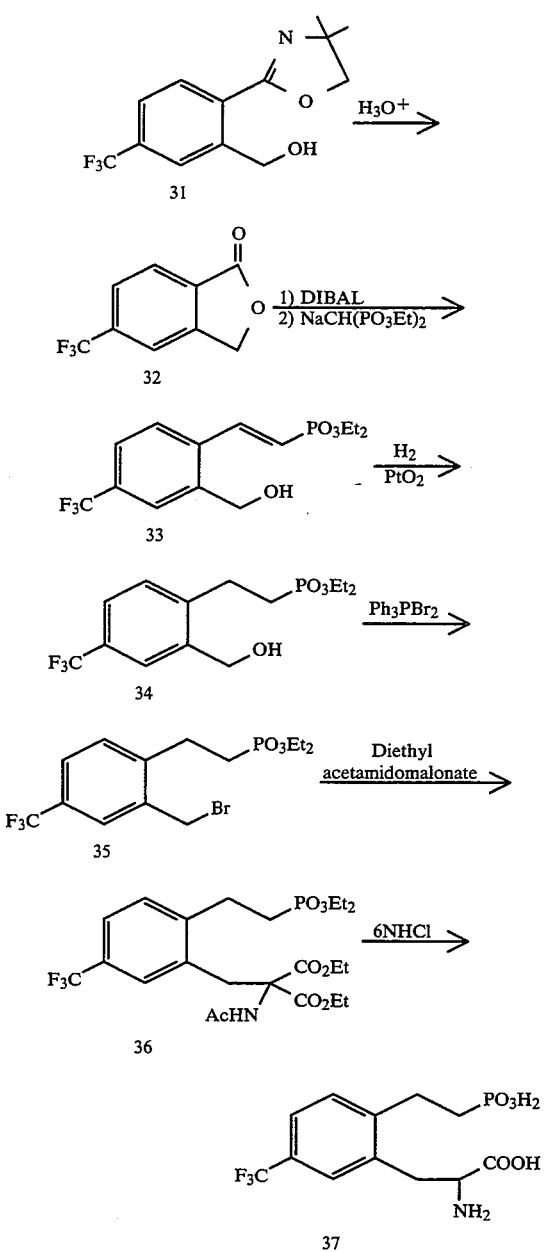

EXAMPLE XXI (Compound 37)

A solution of tetraester 36 (10 mmol) in 6N HCl (100 ml) is refluxed for 24 hours. Removal of the solvent in vacuo furnishes the hydrochloride salt of 37, which is washed with acetone. Liberation of the free amino acid of 37 is accomplished by treating an ethanolic solution of 37 (hydrochloride salt) with propylene oxide. The product 37 thus obtained is washed with acetone and ethanol and dried under vacuum.

N-(2-Methyl-3-hydroxyprop-2-yl)-4-trifluoromethylbenzamide (Compound 29):

A mixture of α, α, α-trifluoro-p-toluic acid (5 g; 26.3 mmol) and 30 ml of thionyl chloride was refluxed for 5 hours. The excess thionyl chloride was evaporated, and the residue was dissolved in methylene chloride (30 ml) and added in a dropwise fashion to a cooled (0° C.) solution of 1-amino-2-methyl-1-propanol (5.43 g; 57.9 mmol) in methylene chloride (30 ml). After the addition was complete the mixture was stirred at room temperature for 1 hour. The reaction mixture was filtered through Celite and concentrated to obtain 6.63 g (96%) of the amide. $^1$H NMR (CDCl$_3$): δ1.42 (s, 6H); 3.71 (s, 2H); 6.46 (br, 1H); 7.68 (d, 2H); 7.83 (d, 2H).

2-(4-Trifluoromethylphenyl)-4,4-dimethyl-2-oxazoline (Compound 30):

Thionyl chloride (10 ml) was added to amide 29 (6.1 g) with stirring in a round bottom flask. After stirring for 2 hours the mixture was treated successively with 10 ml of methanol, 20 ml of saturated sodium bicarbonate, and 10% aqueous NaOH. The product was extracted into ether and the organic phase was dried (MgSO$_4$) and concentrated. The residue was purified on a silica gel column (10% ethyl acetate/hexane) to obtain 4.4 g (83%) of 30. $^1$H NMR (CDCl$_3$): δ1.48 (s, 6H); 4.19 (s, 2H); 7.70 (d, 2H); 8.11 (d, 2H).

2-[(2-hydroxymethyl-4-trifluoromethyl)phenyl]-4,4-dimethyl-2-oxazoline (Compound 31):

Oxazoline 30 (1.6 g; 7.05 mmol) in 15 ml of dry THF at −78° C. was treated with n-butyllithium (7.76 mmol). After 30 minutes paraformaldehyde (490 mg; 15.5 mmol) was added to the mixture and it was allowed to warm to room temperature. After stirring at room temperature for 2 hours the reaction was quenched by the addition of saturated ammonium chloride, the layers were separated, and the organic phase was washed with brine, dried (MgSO$_4$) and freed of solvent. The product was purified on a silica gel column, eluting with 5% ethyl acetate/hexane; there was obtained 1.34 g (30%) of Compound 31. $^1$H NMR (CDCl$_3$): δ1.43 (s, 6H); 4.18 (s, 2H); 4.70 (d, 2H); 6.54 (t, 1H); 7.62 (m, 2H); 7.99 (d, 1H).

5-Trifluoromethylphthalide (Compound 32):

A mixture of oxazoline 31 (1.4 g; 5.0 mmol) and 3N HCl (15 ml) was refluxed for 18 hours. After cooling the product was extracted into ethyl acetate, washed with brine, dried (MgSO$_4$) and concentrated. Purification through a silica gel column (5% ethyl acetate/hexane) delivered 860 mg (85%) of lactone 32 as a white solid, mp 71°–72° C. $^1$H NMR (CDCl$_3$): δ5.42 (s, 2H); 7.82 (d, 2H); 8.08 (d, 1H). IR (KBr): 1761 cm$^{-1}$.

2-[E-(2-diethoxyphosphinyl)ethenyl]-5-trifluoromethylbenzyl alcohol (Compound 33):

Tetraethylmethylenediphosphonate (2.6 g; 8.73 mmol) in THF (7 ml) was added dropwise to a stirred suspension of sodium hydride (288 mg of an 80% suspension; 9.61 mmol) in THF (10 ml). After gas evolution had ceased the mixture was stirred at room temperature for 2 hours and then cooled to −78° C. In a separate flask, a solution of lactone 32 (840 mg; 4.16 mmol) in toluene (20 ml) was cooled to −78° C. and treated with a solution of diisobutylaluminum hydride in toluene (3.32 ml) of a 1.5M solution; 5 mmol). After stirring the mixture for 45 minutes it was quenched by the addition of 30 μl of methanol, and the reaction was added via canula to the solution of phosphonate anion. The resulting mixture was stirred at −78° C. for 4 hours, at which time tert-butyldimethylsilyl chloride (680 mg; 4.37 mmol) in 8 ml of THF was added. The resulting mixture was allowed to come to room temperature overnight. It was quenched by the successive addition of saturated ammonium chloride (15 ml) and 1N HCl (35 ml). The product was extracted into ethyl acetate and the organic phase was washed with brine, dried (MgSO$_4$). Purification by column chromatography (5% ethanol/ethyl acetate) delivered the product as a thick oil.

2-(2-diethoxyphosphinylethyl)-5-trifluoromethylbenzyl alcohol (Compound 34):

A solution of Compound 33 (10 mmol) in ethanol (50 ml) was treated with platinum oxide (200 mg) and hydrogenated at atmospheric pressure at room temperature for 4 hours. The reaction solution was filtered through Celite and concentrated to afford Compound 34 as an oil.

2-(2-diethoxyphosphinylethyl)-5-trifluoromethylbenzyl bromide (Compound 35):

Dibromotriphenylphosphorane (11 mmol) in methylene chloride (35 ml) was added to a solution of alcohol 34 (10 mmol) in methylene chloride (50 ml). This mixture was stirred for 3 hours at room temperature and then partitioned between brine and methylene chloride. The layers were separated and the organic phase was dried (MgSO4) and freed of solvent. The crude material was purified on a silica gel column, eluting with ethyl acetate, to provide bromide 35.

Ethyl 3-[(2-{2-(diethoxyphosphinyl)ethyl}-5-trifluoromethyl)phenyl]-2-carboethoxy-2-acetamidopropanoate (Compound 36):

A mixture of bromide 35 (10 mmol) and diethyl acetamidomalonate (11 mmol) in methylene chloride (20 ml) was added to a solution of tetrabutylammonium hydrogen sulfate (10 mmol) in 10% aqueous NaOH (25 ml). The two phase mixture was stirred for 4 hours, then the layers were separated. The organic phase was washed with brine, dried (MgSO4) and concentrated in vacuo. Chromatography of the residue on silica gel with ethyl acetate afforded tetraester 36.

In the case of the 4-nitro compound, the procedure outlined in Scheme VII is utilized starting with tetraester 38 [W. J. Rzeszotarski, R. L. Hudkins and M. E. Guzewska, U.S. Pat. No. 4,657,899].

The residue thus obtained was filtered, washed with ethanol and dried under vacuum to provide 470 mg (71%) of compound 41 as a white powder, mp>240° C. decomp. $^1$H NMR (D$_2$O/NaOD) : δ1.3–1.5 (m, 2H), 2.6–2.8 (m, 3H), 2.90 (dd, 1H, J=6.75, 13.90 Hz), 3.30 (t, 1H, J=7.19 Hz), 7.28 (d, 1H, J= 9.30 Hz), 7.8–7.9 (m, 2H). IR (KBr): 3700–2100, 1718, 1512, 1352, 923 cm$^{-1}$. Anal. Calcd. for C$_{11}$H$_{15}$N$_2$O$_7$P: C, 41.52; H, 4.75; N, 8.80. Found: C, 41.65; H, 4.77; N, 8.69.

SCHEME VII

Ethyl 3-[(2-{diethoxyphosphinyl}ethyl-4-nitro)phenyl]-2-carboethoxy-2-acetamidopropanoate (39).

A solution of tetraester 38 (4.3 g; 9.13 mmol) in concentrated sulfuric acid (25 mL) was cooled by means of an external ice bath. Potassium nitrate (925 mg; 9.13 mmol) was then added portionwise and the resulting mixture was allowed to gradually warm to room temperature and stirred overnight. The mixture was then poured into ice (200 mL) and extracted with chloroform (3×100 mL). The combined organic layer was dried (MgSO4) and concentrated under reduced pressure. Purification of the residual oil by flash chromatography (silica gel) eluting with hexane/ethyl acetate mixtures afforded 1.95 g of the 4-nitro compound (39) along with 450 mg of the 5-nitro compound (40). $^1$H NMR (CDCl$_3$): δ1.2–1.4 (m, 12H), 1.8–2.1 (m, 5H), 2.9–3.0 (m, 2H), 3.80 (s, 2H), 4.0–4.2 (m, 4H), 4.2–4.4 (m, 4H), 6.62 (s, 1H), 7.37 (d, 1H, J=8.59 Hz), 7.89 (d, 1H, J=2.35 Hz), 8.04 (dd, 1H, J=2.40, 8.53 Hz).

Inhibition of EAA-Induced Currents in Xenopus Oocytes

Defolliculated oocytes obtained from Xenopus laevis females were injected with 30–75 ng of poly (A+) mRNA obtained from 21-day old male Sprague-Dawley rats. Oocytes are placed individually in 100 ml of antibiotic-supplemented modified Barthes solution

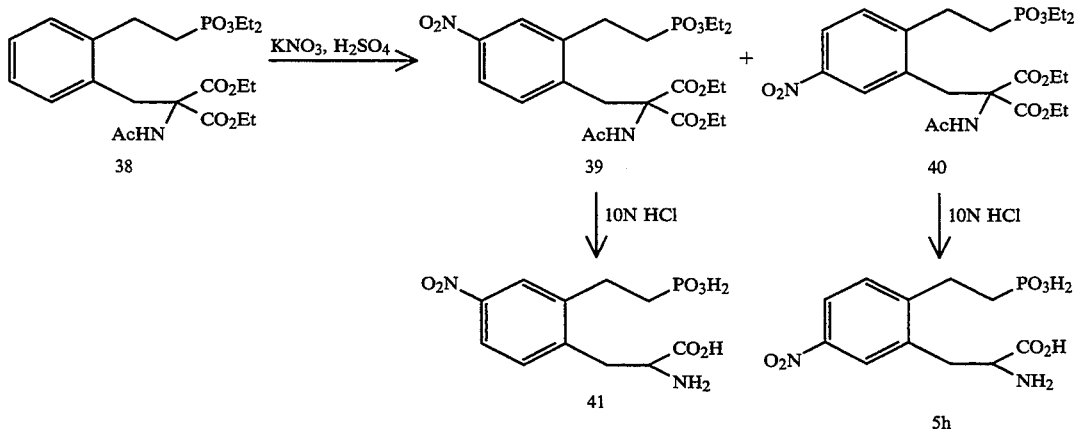

SCHEME VII

EXAMPLE XXII

Synthesis of 4-Nitro-2-(2-phosphonoethyl)phenylalanine (Compound 41):

A solution of tetraester 39 (1.08 g; 2.09 mmol) in 10N HCl (10 mL) was heated at 95° C. for 3 days. Removal of the solvent in vacuo furnished the hydrochloride salt of compound 41, which was washed with water. Liberation of the free amino acid of compound 41 was accomplished by treating an ethanolic solution of compound 41 (hydrochloride salt) with propylene oxide.

(MBS, containing in mM: NaCl, 88; KCl, 1.0; NaHCO$_3$, 2.4; HEPES, 10; MgSO$_4$, 0.82; Ca(NO$_3$)$_2$, 0.33) in 96-well sterile plates and cultured for 48–120 hours prior to experimentation. Oocytes are inspected every 24 hours at which time the bathing solution is replaced with fresh MBS.

For electrophysiological studies, oocytes are positioned in a small recording chamber (500 ml) and superfused with antibiotic-free MBS supplemented with CaCl$_2$ (final concentration=1.4 mM). For NMDA studies, MgSO$_4$ is replaced with NaSO$_4$ (0.55 mM). Oocytes are impaled with a single glass microelectrode, voltage-clamped at −60 to −70 mV, and perfused by gravity feed at a rate of 3–5 ml/min at room temperature. Drugs are dissolved in the perfusate (pH adjusted to 7.3–7.4) and perfused for 1–2 min or until the response has reached a plateau, followed by a 4 min perfusion in the absence of drug(s). Antagonists are coperfused with agonists. MBS used in NMDA assays is prepared from "glycine-free", deionized water.

Potencies to inhibit kainic acid-, AMPA- and NMDA/glycine-induced currents are determined from concentration-response curves. IC$_{50}$ values and Hill coefficients are determined by analysis of indirect Hill plots. IC$_{50}$ values are converted to K$_i$ values for comparison purposes using the Cheng-Prusoff equation.

Compounds of Examples I, II, III, IV, V, VI, and XI each exhibited K$_i$ values less than 100 mM (Table I). The rank order of potency for inhibition of KA-induced currents was Example VI>III=I, ≧IV=II>V. Compounds I–VI were also tested for their ability to inhibit AMPA (100 mM)-induced currents (Table I), producing the following rank order of potencies: I=VI >IV-=II=III. At a concentration of 100 mM, none of the compounds tested produced greater than 50% inhibition of the response to NMDA (100 mM) plus glycine (3 mM) (data not shown).

Protection Against Pentylenetetrazole (PTZ)-Induced Seizures

The anticonvulsant properties of Example I, as well as the reference compound CPP, were evaluated using the mouse (male CF-1, 25–30 g, Harlan Industries) PTZ seizure model. Test compounds were dissolved in saline or the appropriate vehicle and administered either intracerebroventricularly (i.c.v.) in a volume of 5 ml, or intraperitoneally (i.p.) in a volume of 10 ml/kg, thirty minutes prior to subcutaneous (s.c.) administration of PTZ (85 mg/kg). Animals were then placed in individual observation cages and monitored for 30 min for the appearance of clonic convulsions. Failure to observe a clonic convulsion lasting at least 5 sec during the observation period was considered evidence of anticonvulsant activity.

Results of the testing are shown in Table II. Example I provided dose-dependent protection against PTZ-induced seizures, and was nearly 2 times more potent than CPP, a competitive NMDA antagonist, when administered i.c.v. Example I was also effective following systemic administration, but was less potent than CPP under these conditions.

Protection Against Kainic Acid-Induced Striatal Toxicity

Kainic acid-induced lesion studies were performed using rats (male Sprague-Dawley, 200–250 g, Harlan Industries). Animals were anesthetized with Chloropent (1.5 ml/kg) and a cannula was inserted into the corpus striatum at the coordinates A 0.8, V 4.3, L 3.0 (bregma=0) using standard stereotaxic procedures. Compounds were dissolved in dH$_2$O and neutralized using dilute NaOH, and administered over a period of 2 min in a final volume of 2 ml. Following an additional 2 min the cannula was withdrawn, the incision closed with woundclips, and the animals returned to their home cage for a 3 day recovery period. Kainic acid (10 nmoles) was used to induce striatal lesions. Compound XX (300 nmoles) was coadministered with kainic acid.

Following decapitation, the corpus striatum ipsi and contralateral to the injection were removed, immediately frozen on dry ice, and stored at −80° C. until assayed. The activities of choline acetyltransferase (ChAT) and glutamic acid decarboxylase (GAD), markers for striatal cholinergic and GABAergic interneurons, respectively, were determined using standard procedures to assess the extent of the lesion.

Table III shows that intrastriatal injection of kainic acid alone produced reductions of 68% and 55% in ChAT and GAD activity, respectively. In contrast, coadministration of kainic acid with Example I resulted in only a 2% reduction in ChAT activity, and a 12% reduction in GAD activity.

TABLE I

Potencies of example compounds to inhibit KA- and AMPA-induced currents in rat brain mRNA-injected Xenopus oocytes:

| Example | K$_i$ (μM) KA | AMPA |
|---|---|---|
| 15 | >100 | nt |
| 2 | 17 | 50 |
| 12 | 139 | nt |
| 1 | 11 | 13 |
| 11 | 76 | nt |
| 17 | >100 | nt |
| 3 | 10 | 61 |
| 5 | 68 | 167 |
| 4 | 15 | 48 |
| 6 | 3.6 | 16 |
| DNQX | 0.1 | 0.25 |
| 7 | 12 | 39 |
| 10 | 29 | nt |
| 16 | 83 | nt |
| 22 | 13 | nt |

TABLE II

Potencies of Example I and CPP to protect against PTZ-induced seizures:

| Compound (mg/kg) | ED$_{50}$ i.c.v. (nmoles) | i.p. |
|---|---|---|
| Example I | 0.09 | 98 |
| CPP | 0.15 | 7.3 |

PTZ seizure studies were performed as described in the text. ED$_{50}$ values were determined from dose-response curves using at least 6 concentrations of test agent and groups of 6–10 animals per test dose.

TABLE III

Protection against kainic acid-induced striatal toxicity:

| Example | % Activity of Contralateral Striatum ChAT | GAD |
|---|---|---|
| Vehicle | 32 ± 6 | 45 ± 9 |
| I | 98 ± 6 | 88 ± 17 |

Ka-induced lesions were performed as described in the text. The results are expressed as the percentage of enzyme activity in the ipsilateral (injected) striatum relative to enzyme activity in the contralateral (uninjected) striatum. The values represent the mean+standard deviation of 4 (Example I) or 12 (vehicle) determinations.

The invention being thus described, it will be obvious that the same may be varied in many ways. Such variations are not to be regarded as a departure from the spirit and scope of the invention and all such modifications are intended to be included within the scope of the claims.

What is claimed is:

1. A compound having the general formula:

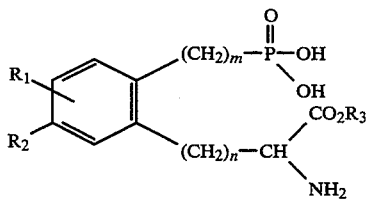

wherein n and m independently are 0, 1, 2, or 3; $R_1$ is selected from the group consisting of hydrogen and $R_2$; $R_2$ is selected from the group consisting of halogen, halomethyl, hydroxyl, methyl and ethyl; $R_3$ is selected from the group consisting of hydrogen, and $C_1$ to $C_6$ lower alkyl; the stereoisomers thereof in their resolved or racemic form, and pharmaceutically acceptable salts thereof; wherein said compound has greater affinity for kainic acid and/or AMPA receptors and lesser or no affinity for other excitatory amino acid receptors.

2. The compound according to claim 1 wherein m is 2.

3. The compound according to claim 1 wherein n is 1.

4. The compound according to claim 1 and being 5-methyl-2-(2-phosphonoethyl)phenylalanine.

5. A compound having the general formula:

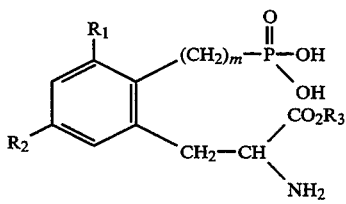

wherein m is 2 or 3; $R_1$ is selected from the group consisting of hydrogen, methyl and halogen; $R_2$ is selected from the group consisting of halogen, halomethyl, hydroxyl, methyl and ethyl; $R_3$ is selected from the group consisting of hydrogen, and $C_1$ to $C_6$ lower alkyl; the stereoisomers thereof in their resolved or racemic form, and pharmaceutically acceptable salts thereof; wherein said compound has greater affinity for kainic acid and/or AMA receptors and lesser or no affinity for other excitatory amino acid receptors.

6. A pharmaceutical composition for relieving pain, which comprises: an effective amount of a compound according to claim 1 together with a pharmaceutically acceptable carrier.

7. A pharmaceutical composition for relieving pain, which comprises: an effective amount of a compound according to claim 5 together with a pharmaceutically acceptable carrier.

8. A pharmaceutical composition for treatment of convulsions or epilepsy, which comprises: an effective amount of a compound according to claim 1 together with a pharmaceutically acceptable carrier.

9. A pharmaceutical composition for treatment of convulsions or epilepsy, which comprises: an effective amount of a compound according to claim 5 together with a pharmaceutically acceptable carrier.

10. A pharmaceutical composition for enhancing cognition, which comprises: an effective amount of a compound according to claim 1 together with a pharmaceutically acceptable carrier.

11. A pharmaceutical composition for enhancing cognition, which comprises: an effective amount of a compound according to claim 5 together with a pharmaceutically acceptable carrier.

12. A pharmaceutical composition for treating psychosis, which comprises: an effective amount of a compound according to claim 1 together with a pharmaceutically acceptable carrier.

13. A pharmaceutical composition for treating psychosis, which comprises: an effective amount of a compound according to claim 5 together with a pharmaceutically acceptable carrier.

14. A pharmaceutical composition for preventing neurodegeneration, which comprises: an effective amount of a compound according to claim 1 together with a pharmaceutically acceptable carrier.

15. A pharmaceutical composition for preventing neurodegeneration, which comprises: an effective amount of a compound according to claim 5 together with a pharmaceutically acceptable carrier.

16. A pharmaceutical composition for treating cerebral ischemic damage, which comprises: an effective amount of a compound according to claim 1 together with a pharmaceutically acceptable carrier.

17. A pharmaceutical composition for treating cerebral ischemic damage, which comprises: an effective amount of a compound according to claim 5 together with a pharmaceutically acceptable carrier.

18. A pharmaceutical composition for treating emesis, which comprises: an effective amount of a compound according to claim 1 together with a pharmaceutically acceptable carrier.

19. A pharmaceutical composition for treating emesis, which comprises: an effective amount of a compound according to claim 5 together with a pharmaceutically acceptable carrier.

* * * * *

UNITED STATES PATENT AND TRADEMARK OFFICE
CERTIFICATE OF CORRECTION

PATENT NO. : 5,395,827
DATED : March 7, 1995
INVENTOR(S) : Rezeszotarski et al.

It is certified that error appears in the above-indentified patent and that said Letters Patent is hereby corrected as shown below:

Claim 5, column 33, line 46, change "AMA" to --AMPA--

Signed and Sealed this

Second Day of May, 1995

Attest:

BRUCE LEHMAN

Attesting Officer

Commissioner of Patents and Trademarks